US009469873B2

(12) United States Patent
Zhao et al.

(10) Patent No.: US 9,469,873 B2
(45) Date of Patent: Oct. 18, 2016

(54) COMPOSITIONS AND METHODS FOR NUCLEOTIDE SEQUENCING

(71) Applicant: Illumina, Inc., San Diego, CA (US)

(72) Inventors: Chanfeng Zhao, San Diego, CA (US); Igor Kozlov, San Diego, CA (US); Melissa Won, Solana Beach, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 14/695,955

(22) Filed: Apr. 24, 2015

(65) Prior Publication Data

US 2015/0225785 A1    Aug. 13, 2015

Related U.S. Application Data

(63) Continuation of application No. 14/327,872, filed on Jul. 10, 2014, now Pat. No. 9,051,612, which is a continuation of application No. 13/846,401, filed on Mar. 18, 2013, now Pat. No. 8,808,988, which is a continuation of application No. 12/442,925, filed as application No. PCT/US2007/019353 on Sep. 4, 2007, now Pat. No. 8,399,188.

(60) Provisional application No. 60/852,388, filed on Oct. 16, 2006, provisional application No. 60/827,388, filed on Sep. 28, 2006, provisional application No. 60/827,395, filed on Sep. 28, 2006.

(51) Int. Cl.
| C07H 17/00 | (2006.01) |
| C07H 19/04 | (2006.01) |
| C07H 21/02 | (2006.01) |
| C12Q 1/68  | (2006.01) |
| C12P 19/34 | (2006.01) |

(52) U.S. Cl.
CPC ............ C12Q 1/6869 (2013.01); C07H 19/04 (2013.01); C12P 19/34 (2013.01); C12Q 1/6823 (2013.01); C12Q 2525/117 (2013.01); C12Q 2525/186 (2013.01); C12Q 2563/107 (2013.01)

(58) Field of Classification Search
CPC .......................... C07H 19/04; C12Q 1/6869
USPC ................. 536/4.1, 23.1, 26.6; 435/6.12
See application file for complete search history.

(56) References Cited

U.S. PATENT DOCUMENTS

| 4,711,955 A | 12/1987 | Ward et al. |
| 4,772,691 A | 9/1988 | Herman |
| 4,824,775 A | 4/1989 | Dattagupta et al. |
| 4,863,849 A | 9/1989 | Melamede |
| 5,118,605 A | 6/1992 | Urdea |
| 5,174,962 A | 12/1992 | Brennan et al. |
| 5,175,269 A | 12/1992 | Stavrianopoulos |
| 5,302,509 A | 4/1994 | Cheeseman |
| 5,328,824 A | 7/1994 | Ward et al. |
| 5,436,143 A | 7/1995 | Hyman |
| 5,449,767 A | 9/1995 | Ward et al. |
| 5,476,928 A | 12/1995 | Ward et al. |
| 5,516,664 A | 5/1996 | Hyman |
| 5,534,424 A | 7/1996 | Uhlen |
| 5,547,839 A | 8/1996 | Dower et al. |
| 5,547,859 A | 8/1996 | Goodman et al. |
| 5,602,000 A | 2/1997 | Hyman |
| 5,763,594 A | 6/1998 | Hiatt et al. |
| 5,770,367 A | 6/1998 | Southern et al. |
| 5,798,210 A | 8/1998 | Canard et al. |
| 5,808,045 A | 9/1998 | Hiatt et al. |
| 5,821,356 A | 10/1998 | Khan et al. |
| 5,849,542 A | 12/1998 | Reeve et al. |
| 5,872,244 A | 2/1999 | Hiatt et al. |
| 5,885,775 A | 3/1999 | Haff et al. |
| 6,001,566 A | 12/1999 | Canard et al. |
| 6,008,379 A | 12/1999 | Benson et al. |
| 6,046,005 A | 4/2000 | Ju et al. |
| 6,074,823 A | 6/2000 | Koster |
| 6,087,095 A | 7/2000 | Rosenthal et al. |
| 6,136,543 A | 10/2000 | Anazawa et al. |
| 6,214,987 B1 | 4/2001 | Hiatt et al. |
| 6,218,118 B1 | 4/2001 | Sampson et al. |
| 6,218,530 B1 | 4/2001 | Rothschild et al. |
| 6,232,465 B1 | 5/2001 | Hiatt et al. |
| 6,242,193 B1 | 6/2001 | Anazawa et al. |
| 6,255,475 B1 | 7/2001 | Kwiatkowski |
| 6,287,821 B1 | 9/2001 | Shi et al. |
| 6,309,836 B1 | 10/2001 | Kwiatkowski |
| 6,312,893 B1 | 11/2001 | Van Ness et al. |

(Continued)

FOREIGN PATENT DOCUMENTS

| DE | 4141178 | 6/1993 |
| EP | 0992511 | 4/2000 |

(Continued)

OTHER PUBLICATIONS

Aso et al. Nucleic Acids Symposium Series No. 48, pp. 59-60, 2004.*

(Continued)

Primary Examiner — Jezia Riley
(74) Attorney, Agent, or Firm — Illumina, Inc.; Yan Leychkis

(57) ABSTRACT

The invention provides nucleoside and nucleotide molecules containing cleavable linkers linking a label such as a dye. The invention also provides nucleosides and nucleotide molecules containing a blocking group, either removable or non-removable. The invention additionally provides methods of using the nucleoside and nucleotide molecules containing a cleavable linker and/or a blocking group.

20 Claims, 18 Drawing Sheets

(56) References Cited

U.S. PATENT DOCUMENTS

| | | | |
|---|---|---|---|
| 6,380,378 B1 | 4/2002 | Kitamura et al. |
| 6,524,829 B1 | 2/2003 | Seeger |
| 6,613,508 B1 | 9/2003 | Ness et al. |
| 6,639,088 B2 | 10/2003 | Kwiatkowski |
| 6,664,079 B2 | 12/2003 | Ju et al. |
| 6,780,591 B2 | 8/2004 | Williams et al. |
| 6,787,308 B2 | 9/2004 | Balasubramanian et al. |
| 6,911,345 B2 | 6/2005 | Quake et al. |
| 6,982,146 B1 | 1/2006 | Schneider et al. |
| 7,037,687 B2 | 5/2006 | Williams et al. |
| 7,056,666 B2 | 6/2006 | Dower et al. |
| 7,057,026 B2 | 6/2006 | Barnes et al. |
| 7,057,031 B2 | 6/2006 | Olenjnik et al. |
| 7,074,597 B2 | 7/2006 | Ju |
| 7,078,499 B2 | 7/2006 | Odedra et al. |
| 7,105,300 B2 | 9/2006 | Parce et al. |
| 7,169,560 B2 | 1/2007 | Lapidus et al. |
| 7,414,116 B2 | 8/2008 | Milton et al. |
| 7,427,673 B2 | 9/2008 | Balasubramanian et al. |
| 7,459,275 B2 | 12/2008 | Dower et al. |
| 7,553,949 B2 | 6/2009 | Lee et al. |
| 8,399,188 B2 | 3/2013 | Zhao et al. |
| 8,808,988 B2 | 8/2014 | Zhao |
| 2003/0008285 A1 | 1/2003 | Fischer |
| 2003/0186256 A1 | 10/2003 | Fischer |
| 2003/0194722 A1* | 10/2003 | Odedra ............... C07H 19/10 435/6.11 |
| 2004/0014096 A1 | 1/2004 | Anderson et al. |
| 2004/0096825 A1 | 5/2004 | Chenna et al. |
| 2004/0185466 A1 | 9/2004 | Ju et al. |
| 2005/0037398 A1 | 2/2005 | Gelfand et al. |
| 2005/0037991 A1 | 2/2005 | Bodepudi |
| 2005/0042648 A1 | 2/2005 | Griffiths et al. |
| 2005/0079510 A1 | 4/2005 | Berka et al. |
| 2006/0188901 A1 | 8/2006 | Barnes et al. |
| 2006/0199198 A1 | 9/2006 | Brenner |
| 2007/0166705 A1 | 7/2007 | Milton et al. |

FOREIGN PATENT DOCUMENTS

| | | |
|---|---|---|
| EP | 1182267 | 2/2002 |
| EP | 1291354 | 3/2003 |
| EP | 0808320 | 4/2003 |
| EP | 1451351 | 9/2004 |
| EP | 1530578 | 5/2005 |
| EP | 1560838 | 8/2005 |
| EP | 1730307 | 12/2006 |
| EP | 1337 541 | 3/2007 |
| EP | 1218391 | 4/2007 |
| EP | 1790736 | 5/2007 |
| WO | 89/09282 | 10/1989 |
| WO | 90/13666 | 11/1990 |
| WO | 91/06678 | 5/1991 |
| WO | 92/10587 | 6/1992 |
| WO | 93/05183 | 3/1993 |
| WO | 93/21340 | 10/1993 |
| WO | 94/14972 | 7/1994 |
| WO | 96/07669 | 3/1996 |
| WO | 96/23807 | 8/1996 |
| WO | 96/27025 | 9/1996 |
| WO | 98/30720 | 7/1998 |
| WO | 99/05315 | 2/1999 |
| WO | 99/57321 | 11/1999 |
| WO | 00/02895 | 1/2000 |
| WO | 00/06770 | 2/2000 |
| WO | 00/15844 | 3/2000 |
| WO | 00/18956 | 4/2000 |
| WO | 00/21974 | 4/2000 |
| WO | 00/50642 | 8/2000 |
| WO | 00/53805 | 9/2000 |
| WO | 00/53812 | 9/2000 |
| WO | 00/70073 | 11/2000 |
| WO | 01/16375 | 3/2001 |
| WO | 01/23610 | 4/2001 |
| WO | 01/25247 | 4/2001 |
| WO | 01/32930 | 5/2001 |
| WO | 01/57248 | 8/2001 |
| WO | 01/57249 | 8/2001 |
| WO | 01/92284 | 12/2001 |
| WO | 02/02813 | 1/2002 |
| WO | 02/22883 | 3/2002 |
| WO | 02/29003 | 4/2002 |
| WO | 02/072892 | 9/2002 |
| WO | 02/079519 | 10/2002 |
| WO | 02/088381 | 11/2002 |
| WO | 02/088382 | 11/2002 |
| WO | 03/002767 | 1/2003 |
| WO | 03/020968 | 3/2003 |
| WO | 03/048178 | 6/2003 |
| WO | 03/048387 | 6/2003 |
| WO | 03/085135 | 10/2003 |
| WO | 2004/007773 | 1/2004 |
| WO | 2004/018493 | 3/2004 |
| WO | 2004/018497 | 3/2004 |
| WO | 2004/055160 | 8/2004 |
| WO | 2005/010145 | 2/2005 |
| WO | 2005/084367 | 9/2005 |
| WO | 2005/118608 | 12/2005 |
| WO | 2005118608 | 12/2005 |
| WO | 2007/002204 | 1/2007 |
| WO | 2007/053702 | 5/2007 |
| WO | 2007/053719 | 5/2007 |
| WO | 2007/075967 | 7/2007 |

OTHER PUBLICATIONS

U.S. Appl. No. 90/008,152, filed Aug. 3, 2006, Gitten.
U.S. Appl. No. 90/008,149, filed Aug. 4, 2006, Gitten.
Anonymous, , "Gene Characterization Kits", p. 39, Stratagene Catalog (1988), 1988, 39.
Bergmann, et al., "Allyl as internucleotide protecting group in DNA synthesis to be cleaved off by ammonia", Tetrahedron NL vol. 51 No. 25, 1995, 6971-6976.
Brunckova, et al., "Intramolecular Hydrogen Atom Abstraction in Carbohydrates and Nucleosides: Inversion of an ****", Tetrahedron Letters 35, 1994, 6619-6622.
Burgess, et al., "An approach to Photolabile, Fluorescent Protecting Groups", J Org. Chem, 62:5165-5168 (1997), 1997, 5165-5168.
Buschmann, et al., "Spectroscopic Study and Evaluation of Red-Absorbing Fluorescent Dyes", Bioconjugate Chem. 14: 195-204 (2003), 2003, 195-204.
Canard, et al., "Catalytic editing properties of DNA polymerases", Proc. Natl. Acad. Sci., vol. 92, 1995, 10859-10863.
Canard B. and, Sarfati R.S , "DNA polymerase fluorescent substrates with reversible 3'-tags", Gene, 1994, p. 1-6, vol. 148., 1994, 1-6.
Crespo-Hernandez, et al., "Part 1. Photochemical and Photophysical Studies of Guanine Derivatives: Intermediates Contributing to its Photodestruction Mechanism in Aqueous solution and the participation of the Electron Adduct,", Photochemistry and Photobiology, 71(5):534-543 (2000), 2000, 534-543.
Dressman, et al., "Transforming single DNA molecules into fluorescent magnetic particles for detection and enumeration of genetic variations", PNAS, 100(15), 2003, 8817-8822.
Greene, , "Protective groups in organic synthesis", John Wiley & Sons NY, 1999, 67-74 & 574-576.
Greene, et al., "Protective Groups in Organic Synthesis", John Wiley & Sons, New York, 1991, 42-45, and 417.
Guibe, et al., "Allylic Protecting Groups adn their use in a complex environment part I: Allylic Protection of Alcohols", Tetrahedron NL vol. 53 No. 40, 1997, 13509-13556.
Guibe, et al., "Allylic Protecting Groups and their use in a complex environment part II: Allylic protecting groups and their removal through Catalytic Palladium pi-Allyl Methodology", Tetrahedron NL vol. 54 No. 13, 1998, 2967-3042.
Hayakawa, et al., "O-Allyl protection of guanine and thymine residues in oligodeoxyribonucleotides", J of Organometallic Chemistry, CH vol. 58, 1993, 5551-5555.

(56) References Cited

OTHER PUBLICATIONS

Henner, et al., "Enzyme Action at 3' Termini of Ionizing Radiation-induced DNA Strand Breaks", The Journal of Biologicial Chemistry: 258, 1983, 15198-15205.

Hovinen, Jari et al., "Synthesis of 3' . . . ", JCS Perkin Trans 1, 1994, 211-217.

Ikeda, et al., "A non-radioactive DNA Sequencing Method Using Biotinylated Dideoxynucleoside Triophospates and ΔTth DNA Polymerase", 2:225-227 (1995), 1995, 225-227.

Kamal, et al., "A mild and rapid regeneration of Alcohols from their Allylic Ethers by Chlorotrimethylsilane/Sodium Iodide", Tetrahedron Letters vol. 40, 1999, 371-372.

Kitamura, et al., "(P ( C6H5) 3) CpRu+-Catalyzed Deprotection of Allyl Caboxylic Esters", JOC, American Chemistry Society vol. 67 No. 14, 2002, 4975-4977.

Kloosterman, et al., "The Relative stability of Allyl Ether, Allyloxycarbonyl Ester and prop-2 Enylidene acetal protective groups toward iridium, rhodium and palladium catalysts", Tetrahedtron letters NL vol. 26 No. 41, 1985, 5045-5048.

Knapp, Diana , Poster presented at International Roundtabel on Nucleosides, Nucleotides, and Nucleic Acids (Bern, Switzerland; Sep. 2006).

Kocienski, , "Protecting groups", Georg Tieme Verlag, Stuttgart, 1994, 61-68.

Kraevskii, et al., "Substrate Inhibitors of DNA Biosynthesis", Molecular Biology 21, 1987, 25-29.

Krecmerova, et al., "Synthesis of 5'-O-Phosphonomethyl Derivatives of Pyrimidine 2'-Deoxynucleosides", Coll Czech Chem comm No. 55, 1990, 2521-2536.

Kurata, et al., "Fluorescent quenching-based quantitative detection of specific DNA/RNA using a BODIPY ( (R) ) FL-labeled probe or primer", Nucleic Acids Research , GB vol. 29 No. 6, 2001, E34.

Kvam, et al., "Characterization of singlet oxygen-induced guanine residue damage after photochemical treatment of free nucleosides and DNA", Biochimica et Biophysica Acta., 1217: 9-15 (1994), 1994, 9-15.

Li, et al., "A photocleavable fluorescent nucleotide for DNA sequencing and analysis,", Proc. Natl. Acad. Sci. 100:414-419 (2003), 2003, 414-419.

Maier, et al., "Synthesis and Properties of New Fluorescein-Labeled Oligonucleotides", Nucleosides & Nucleotides 14, 1995, 961-965.

Markiewicz, et al., "A new method of synthesis of fluorescently labelled oligonucleotides and their application in DNA sequencing", Nucleic Acids Research 25, 1997, 3672-3680.

Marquez, et al., "Selective Fluorescence Quenching of 2,3-Diazabicyclo(2.2.2)oct-2-ene by Nucleotides", Organic Letters, 5:3911-3914 (2003), 2003, 3911-3914.

Metzker, , "Termination of DNA synthesis by novel 3'-modified-deoxyribonucleoside 5'-triphosphases", Nucleic Acids Research, vol. 22(20), 1994, 4259-4267.

Nazarenko, et al., "Effect of primary and secondary structure of oligodeoxyribonucleotides on the fluorescent properties of conjugated dyes", Nucleic Acids Research, vol. 30, No. 9, 2002, 2089-2095.

Nishino, et al., "Efficient Deanilidation of Phosphoranilidates by the Use of Nitrites and Acetic /Anhydride", Heteroatom Chemistry vol. 2, 1991, 187-196.

Olejnik, et al., "Photocleavable biotin derivatives: A versatile approach for the isolation of biomolecules", Proc Natl. Acad. Sci. 92:7590-7594 (1995), 1995, 7590-7594.

Quaedflieg, et al., "An Alternative Approach towards the Synthesis of (3'-5') methylene Acetal Linked Dinucleosides", Tetrahedron letters, 33:, 1992, 3081-3084.

Rao, et al., "Four Color Fret dye nucleotide terminators for DNA sequencing", Nucleosides, Nucleotides & Nucleic Acids vol. 20, 2001, 673-676.

Rasolonjatovo, et al., "6-N-(N-Methylanthranylamido)-4-Oxo-Hexanoic Acid : A New Fluorescent Protecting Group Applicable to a New DNA Sequencing Method", Nucleosides & Nucleotides, 17:2021-2025 (1998), 1998, 2021-2025.

Sarfati, et al., "Synthesis of fluorescent derivatives of 3'-O-(6-aminohexanoyl)-pyrimidine nucleosides 5Å?-triphosphates that act as DNA polymerase substrates reversibly tagged at C-3'", JCS Perkin Trans, 1995, 1163-1171.

Seeger, , "Translation: Single Molecule Fluorescence: High performance Molecular diagnosis & screening", Bioforum Git Verlag DE vol. 21 No. 4, 1998, 1-4.

Tawfik, et al., "Man-made Cell-like Compartments for Molecular Evolution", Nature Biotechnology, 16(7), 1998, 652-656.

Torimura, et al., "Fluorescence-Quencing Phenomenon by Photoinduced Electron Transfer between a Fluorescent Dye and Nucleotide Base", Analytical Sciences, 17:155-160 (2001), 2001, 155-160.

Veeneman, et al., "An efficient approach to the synthesis of thymidine derivatives containing phosphate-isosteric methylene acetal linkages", Tetrahedron vol. 47, 1991, 1547-1562.

Wada, et al., "2-(Azidomethyl)benzoyl as a new protecting group in nucleosides,", Tetrahedron Letters, 42, 2001, 1069-1072.

Welch, et al., "Syntheses of Nucleosides Designed for Combinatorial DNA Sequencing", Chemistry, European Journal, 5:951-960 (1999), 1999, 951-960.

Yamashita, et al., "Studies of Antitumor Agents, VII. Antitumor Activities of O-Alkoxyalkyl Derivatives of 2'-Deoxy-5-trifluoromethyluridine", Chem Pharm Bull, 35, 1987, 2373-2381.

Zavgorodny, et al., "1-Alkylthioalkylation of Nucleoside Hydroxyl Functions and its synthetic applications", Tetrahedron Letters vol. 32 No. 51, 1991, 7593-7596.

Zavgorodny, et al., "S,X-Acetals in Nucleoside Chemistry III. Synthesis of 2' and 3' O-Azidomethyl Derivatives of Ribonucleosides", Nucleosides, Nucleotides & Nucleic Acids 19, 2000, 1977-1991.

\* cited by examiner

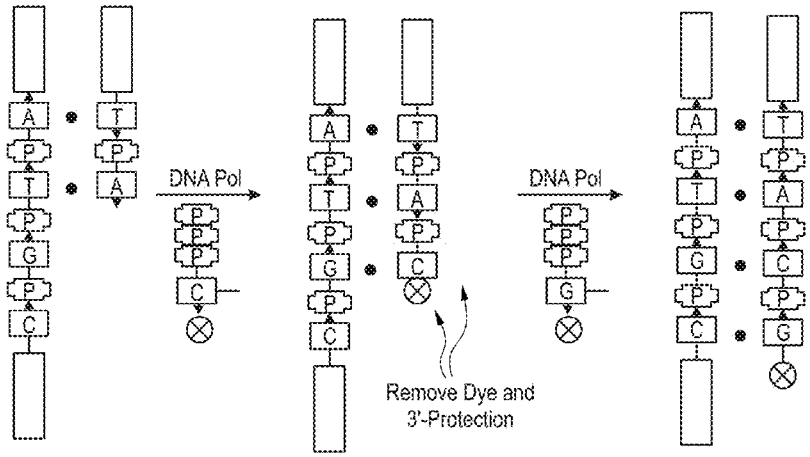
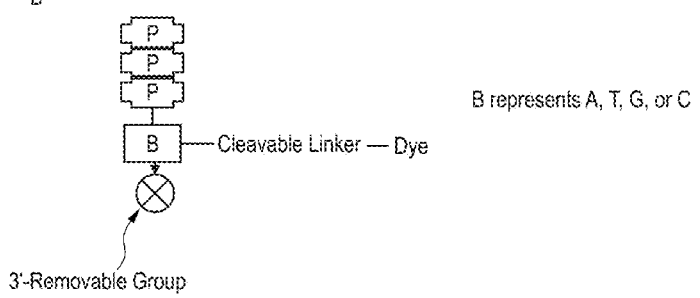
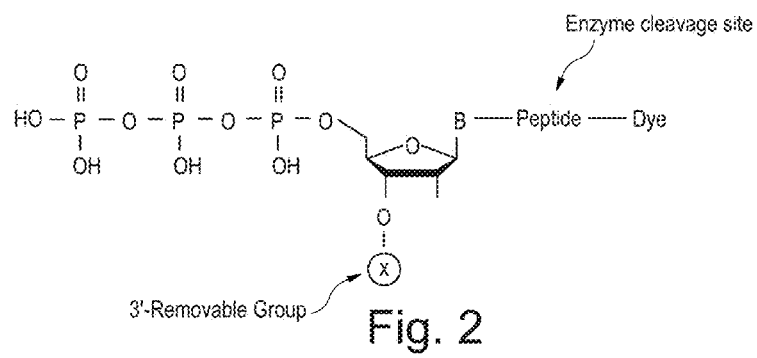
Fig. 2

Finding the Best Peptide Linker

We have generated the cleavage data for Subtilisin A and Chymotrypsin proteases for about 1000 different peptides. The top 10 peptides were selected for further evaluation.

| # | Peptide Name | Peptide Sequence | |
|---|---|---|---|
| 1 | P1 | HHHHHLLVYGGGGbiotin | |
| 2 | P2 | HHHHHLNAGFTASbiotin | |
| 3 | P3 | HHHHHSLAYYTAGbiotin | |
| 4 | P4 | HHHHHITVQTVTWbiotin | |
| 5 | P5 | HHHHHLGLARGGGbiotin | |
| 6 | P6 | HHHHHLGRLVVYbiotin | |
| 7 | P7 | HHHHHATVLTVALbiotin | ← The best performing peptide |
| 8 | P8 | HHHHHSQNYVTVGbiotin | |
| 9 | P9 | HHHHHIEPRSFSQbiotin | |
| 10 | P10 | HHHHHLSPRTFHPbiotin | |
| 11 | P11 | HHHHHHGAGA | |
| 12 | No peptide | | |

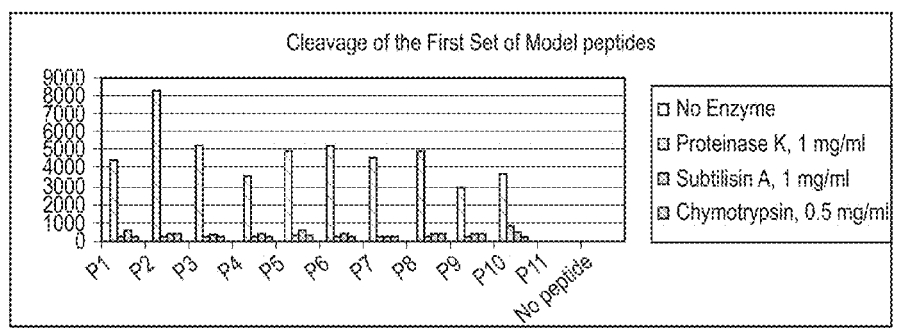

Fig. 3

Incorporation on the Array
1) No enzyme
2) + dTTP
3) + dTTP, dATP, dCTP, dGTP
4) + Biotinylated dUTP
5) + Biotinylated dUTP + dATP, dCTP, dGTP
6) + FAM-dUTP
7) + FAM-dUTP + dATP, dCTP, dGTP
8) + Amine-dUTP
9) + Amine-dUTP + dATP, dCTP, dGTP
10) + Aldehyde-dUTP
11) + Aldehyde-dUTP + dATP, dCTP, dGTP
12) + Hydrazine-dUTP
13) + Hydrazine-dUTP + dATP, dCTP, dGTP
14) + Unlabeled primers + FAM-dUTP
15) + Unlabeled primers + FAM-dUTP, dATP, dCTP, dGTP Sample from Lane 6 of gel A, cleaved with Protease, 1 min.
16) + FAM-dUTP
17) + FAM-dUTP + cleaved with protease, 1 minute R/T in the presence of 95% formamide

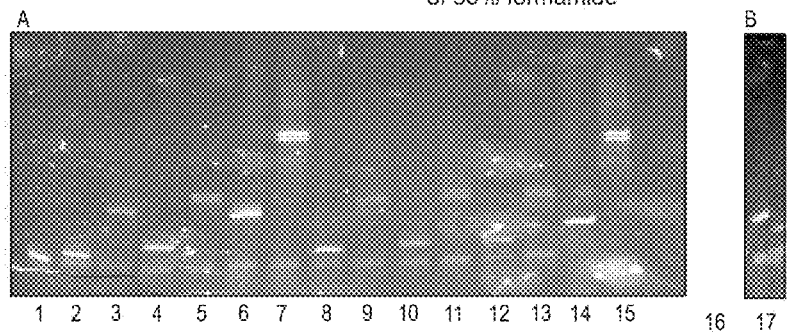

Fig. 8

Incorporation on the Array
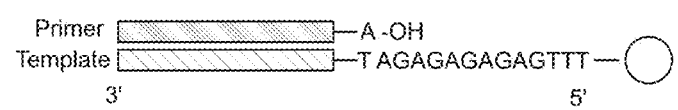
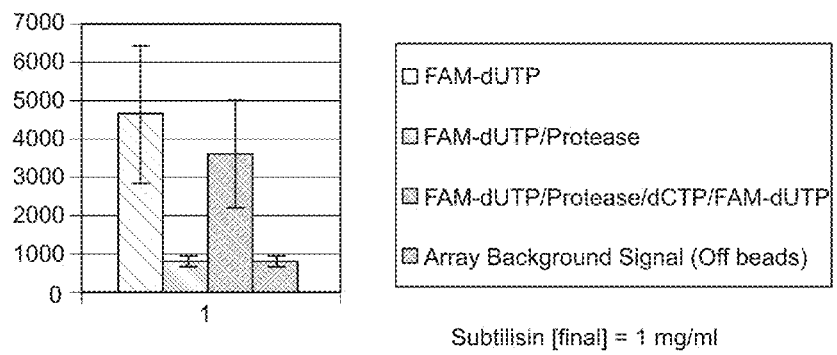
Fig. 9

COMPOSITIONS AND METHODS FOR NUCLEOTIDE SEQUENCING

BACKGROUND OF THE INVENTION

This invention relates generally to methods for analysis of nucleic acids and, more specifically to genomic sequence analysis useful in personalized medical analysis.

The diagnosis and treatment of human diseases continues to be a major area of social concern. The importance of improving health care is self evident, so long as there continues to be diseases that affect individuals, there will be an effort to understand the cause of such diseases as well as efforts to diagnose and treat such diseases. Preservation of life is an inherent force motivating the vast amount of time and expenditure continually invested into scientific discovery and development processes. The application of results from these scientific processes to the medical field has led to surprising advancements in diagnosis and treatment over the last century, and especially over the last quarter century. Such advancements have improved both the quality of life and life span of affected individuals.

However significant m both scientific and medical contribution to their respective fields, the progression of advancements have been slow and painstaking, generally resulting from step-wise trial and error hypothesis driven research. Moreover, with each advancement there can be cumulative progression in the overall scientific understanding of a problem, but there are few guarantees that the threshold needed to translate a discovery into a practical medical application has been achieved. Additionally, with the achievement of all too many advancements comes the sobering realization that the perceived final answer for a complete understanding of a particular physiological or biochemical process is, instead, just a beginning to a more complex process still needed to be dissected and understood.

Further complicating the progression of scientific advancements and its practical application can result from technical limitations in available methodology. Each discovery or advancement can push the frontiers of science to new extremes. Many times, continued progress can be stalled due to the unavailability or insufficiency in technological sophistication needed to continue studies or implement practical applications at the new extremes. Therefore, further advancements in the scientific discovery and medical fields necessarily have to await progress in other fields for the advent and development of more capable technologies and materials. As a result, the progression of scientific advancements having practical diagnostic and therapeutic applications can occur relatively slowly because it results from the accumulation of many smaller discoveries, contributions and advancements in technologies.

Genomic technology has been one such scientific advancement purported to open new avenues into the discovery and development processes and achieve new dimensions in the medical diagnostic and therapeutic fields. Genomic research has resulted in the sequencing of numerous whole genomes, including human. Futuristic speculation of genomic technology for medical applications has been directed to revolutionary diagnostic applications because of the precise physical characteristics purportedly available from complete genome sequences.

However, except for certain nucleic acid detection procedures amenable to selected targets, application of the vast amount of genomic information, and technology to medical diagnosis and treatment is still in its infancy. One drawback hindering the application of genomics to practical medicine is due to the inability to select relevant sequences among a vast amount of non-informative sequences for analysis. In effect, the wheat cannot be sufficiently separated from the chaff prior to analysis, which leads to bias in the results.

For examples one problem with many nucleic acid selection methods is the loss of an accurate sequence representation in the selected population compared to the authentic genomic population. Selection methods amenable to medical applications generally amplify specific regions of the nucleic acids using a variety of methods including, for example, PCR, rolling circle, TMA, NASBA and the like. However, batch amplification needed for high throughput genomic applications results in significant distortion of the resulting sequence representation compared to the original mixture.

An alternative method for selecting nucleic acids from complex genomic mixtures employs destruction of the unwanted nucleic acid. These methods often rely on chemistries of specific bases or sequences and have limited applicability to large scale and/or high throughput analysis because of their inability to target any region of the genome. Therefore, while spectacular in its potential ramifications, the ability to accurately sort through, select and identify relevant genomic sequences among other genomic sequences in complex genomic DNA mixture has failed to allow application of this technology to achieve its potential. Furthermore, for personalized medicine, more rapid and less expensive techniques for genome analysis are required. In particular, it would be beneficial to develop techniques that would allow rapid, efficient and cost effective sequencing of genomic DNA. Such techniques would also be useful in diagnostics, for example, identification of microorganisms such as viruses, bacteria or bacterial strains, in particular virulent bacterial or viral strains, as well as forensic applications.

Thus, there exists a need for more rapid and efficient methods for accurately sequencing nucleic acids such as genomic DNA. The present invention satisfies this need and provides related advantages as well.

The invention provides nucleoside and nucleotide molecules containing cleavable linkers linking a label such as a dye. The invention also provides nucleosides and nucleotide molecules containing a blocking group, either removable or non-removable. The invention additionally provides methods of using the nucleoside and nucleotide molecules containing a cleavable linker and/or a blocking group.

BRIEF DESCRIPTION OF THE DRAWINGS

FIG. 2 shows the scheme for sequencing by synthesis (SBS) using nucleotides with enzymatically cleavable linkers. A schematic drawing of an SBS method is shown.

FIG. 2 also shows a proposed structure of a nucleotide having an enzymatically cleavable linker. The nucleotide contains a removable group at the 3' position and the dye linked to the nucleotide via a peptide that is cleavable by a protease.

FIG. 3 shows exemplary peptide linkers and the results of cleavage of those linkers with proteinase K, subtilisin and chymotrypsin.

FIG. 8 shows gel analysis of the incorporation of modified dUTPs.

FIG. 9 shows incorporation of FAM-dUTP on a BeadArray™.

DETAILED DESCRIPTION OF THE INVENTION

One of the key challenges of sequencing by synthesis (SBS) is to identify a set of modified nucleotides (dATP, dGTP, dTTP, dCTP) as reversible terminators, which can be incorporated by polymerases efficiently and the blocking group removed readily after incorporation. Almost all the reported reversible terminators for SBS are modified at the 3'-OH position of 2'-deoxynucleoside triphosphates. However, the 3' modification of deoxynucleoside triphosphates inhibits the activity of most polymerases. A few 3' modified nucleotides with small modifiers, like the allyl group, have been shown to be accepted by polymerases that are engineered to include mutations in their nucleotide binding sites.

Figure 1:
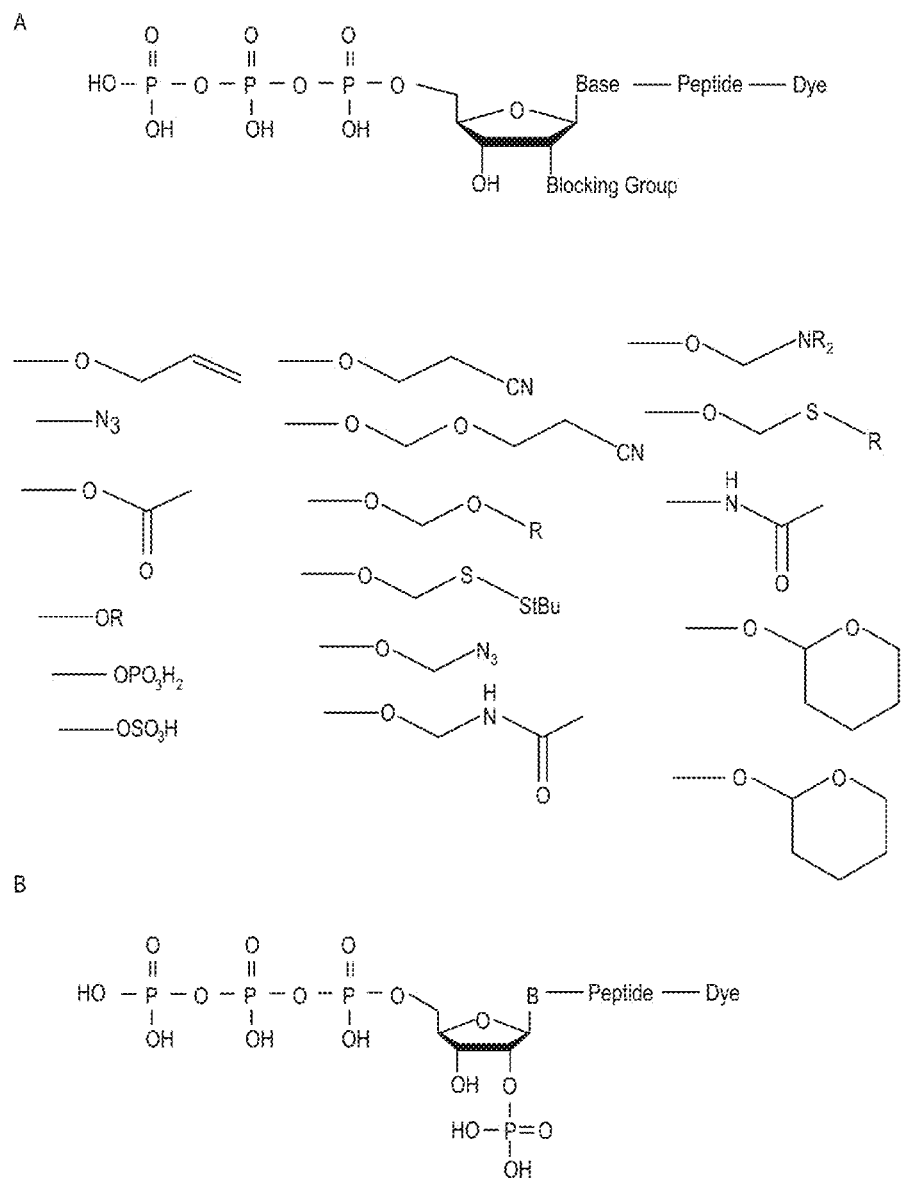
FIG. 1 shows the structure of an exemplary 2'-modified nucleotide for use as a reversible terminator in a sequencing by synthesis (SBS) method along with exemplary 2' blocking groups, and shows a 2' reversible terminator with a phosphate as the blocking group.

As disclosed herein, a blocking group can be placed at an alternate position of a nucleotide, such as 2' or 4', such that the nucleotide is efficiently incorporated but also effectively blocks incorporation of the next nucleotide. These blocking groups might have properties such as charge, hydrophobicity, hydrophilicity, or size. The properties are such that the blocking group effectively terminates the polymerase reaction but allows sufficient recognition and efficient incorporation of the modified nucleotide into a nucleotide sequence by the polymerase. The blocking group can subsequently be removed. Such modified nucleotides are referred to herein as a 2' or 4' reversible terminator. Exemplary 2' reversible terminators and blocking groups are shown in FIG. 1A. Additionally, a sulfate group can also be used as a blocking group. Other blocking groups suitable for a 2' or 4' reversible terminator include but are not limited to allyl, acetal, aminal and thial groups. Following incorporation of these terminators by a polymerase such as a DNA polymerase in an SBS approach, the terminators can be removed, for example, photolytically, chemically or enzymatically. The atom attached to the C2' carbon atom in FIG. 1A, or to the C4' carbon atom of a 4' reversible terminator, does not have to be oxygen since the only requirement is that the change induced during the deblocking step should transform the incorporated terminator nucleotide into a nucleotide that can be further extended. It is understood that the exemplary blocking groups described herein as 2' blocking groups can also be used as 4' blocking groups for a 4' reversible terminator of the invention.

As disclosed herein, a 2' blocking group can be used as a removable group for any primer extension method such as SBS. A particularly useful 2' blocking group is a phosphate group, which is negatively charged and bulky enough that it can act as a terminator. Moreover, many potential reversible terminators can be used in an SBS approach. There are many potential removable blocking groups that can be selected, including but not limited to those shown in FIG. 1A. For example, the phosphate group can be removed completely by alkaline phosphatase in less than 10 minutes or even less than a minute in aqueous solution (see Example II). Thus, the phosphate group can be removed under conditions which preserve hybridization of the primer to the target DNA. Such a 2' modified nucleotide useful in SBS is shown in FIG. 1B.

Figure 14:
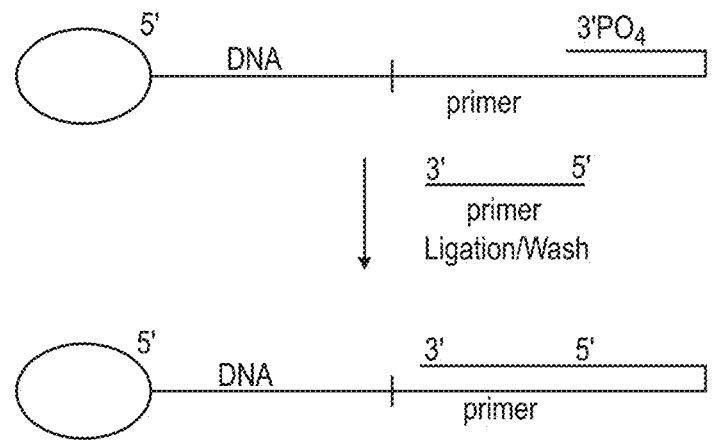
FIG. 14 shows an exemplary method of making beads with a hairpin structure.

In addition to the phosphate group, there are many other potential reversible terminators which can be used in a primer extension method. Blocking groups that can be used as reversible terminators include, but are not limited to, those shown in FIG. 1A. Particularly useful conditions for removing the terminator moiety include those which preserve hybridization of the primer to the target DNA. However it may also be possible to use additional methods which require a hairpin to link the primer covalently to the target DNA. For example, a primer can include a palindromic sequence that allows formation of a hairpin structure. The 5' end of the primer can be covalently attached to the 3' end of a target nucleic acid such that formation of the hairpin structure provides a 3' end that can be extended using the target nucleic acid as a template. The advantage of using a hairpin primer-target nucleic acid species is that although some of the conditions to which the species may be exposed result in denaturation of the template hybrid, the species can be exposed to hybridizing conditions and the hairpin will readily reform, allowing primer extension to proceed. An exemplary hairpin structure useful for SBS or other primer extension methods is shown in FIG. 14.

In a particular embodiment, all four reversibly 2'-blocked ribonucleotides (ATP, GTP, CTP, UTP) containing a phosphate, or other cleavable group at the 2' position, and a dye attached to the base will be used in each cycle of SBS. Each nucleotide base has a unique fluorescent color (dye) associated with it. This dye is linked to the base through a chemically- or enzymatically-cleavable linker. Although generally described herein using a cleavable linker, it is understood that a cleavable linker is not required so long as the signal from the dye attached to nucleic acid molecule can be reduced. For example, the signal from a dye can be reduced by chemical quenching, thermal quenching, photo-bleaching and the like. The dye can also be removed or modified by cleaving the dye while leaving the linker intact, so long as the detectable signal from the dye is reduced sufficiently to allow identification of a subsequently added dye molecule to an extended nucleic acid chain. For example, as disclosed herein, a protease-cleavable peptide linkage can be used. At each polymerase extension cycle, only one nucleotide will be incorporated. A fluorescent image is taken to determine which base has been incorporated based on the color codes. In a particularly useful embodiment, the dye molecules can be cleaved by a protease through a peptide bond, and the phosphate group can be subsequently removed using a phosphatase such as alkaline phosphatase. If desired, the cleavage reaction to remove the dye and the reaction to remove the blocking group can be carried out at the same time. This is particularly useful if both reactions are enzymatic reactions and can be carried out in the same buffer, for example, when using peptide cleavage and phosphatase cleavage for removing the dye and blocking group, respectively. Once the dye and blocking groups are removed, a new SBS cycle starts again.

At least three properties of the blocked ribonucleotides favor increased read length for the SBS process, including 1) they can be incorporated by polymerase enzyme efficiently with great fidelity; 2) the blocking group is able to sufficiently block the next nucleotide's incorporation; 3) the blocking group can be readily removed under mild conditions. Particularly useful mild conditions for removing the blocking group include in an aqueous solution at room temperature. In general, mild conditions are those that do not adversely affect the reagents used in the sequencing methods or products produced by the methods. Mild conditions also include those that can be readily altered to achieve conditions desired for subsequent steps of a sequencing method. Almost all the previously reported reversible terminators are 3' modified, where a blocking group is added onto the 3'-OH group. A disadvantage of 3' modification can be that enzyme activity is often inhibited by the blocking group. Mutations to the polymerase often allow for incorporation, but to date, incorporation of 3' modified nucleotides by these modified enzymes does not exhibit the efficiency or fidelity of natural polymerases with natural nucleotides.

As disclosed herein, a reversible blocking group occurs at the 2' or 4' position on the sugar ring. These positions are close to the 3'-hydroxyl group but allow for improved binding to the polymerase since polymerases have strict requirements for the 3'-OH binding pocket. Locked nucleic acid (LNA) nucleotides that are 2'- and 4'-blocked are also useful. It is possible that polymerases can be evolved and modified for improved recognition of LNA nucleotides, if desired.

There are at least two reasons for using phosphate as a blocking group for the 2'- and 4'-positions: 1) initial studies using 3' phosphate modified nucleotides showed that the negatively charged phosphate group was too bulky to be incorporated by all 5 tested enzymes, Sequenase™ (USB), Klenow, Therminator™ (New England Biolabs), KlenThermase (GeneCraft, Germany), Therminator 2 (New England Biolabs); and 2) the phosphate group can be quantitively removed using alkaline phosphatase in less than a minute in aqueous buffer at room temperature.

PCT publication WO 2005/005667 describes using a 2' modified nucleotide as terminator in a method similar to the Sanger sequencing approach. In the reference, it was claimed that the 2' modified nucleotide could be incorporated by enzymes. Thus, use of a 2' reversible terminator for SBS methods will provide an advantage of a nucleotide that can readily be incorporated into a growing nucleic acid in such a way that a single position is added between steps to remove 2' blocking groups.

The present invention also relates to methods for sequencing by synthesis (SBS) using an enzymatically cleavable linker. This invention suggests a new way for the fluorescent dye removal in the DNA sequencing by synthesis approach (FIG. 2A). An enzymatically cleavable linker group is introduced between a dye residue and nucleobase in nucleoside triphosphates (FIG. 2B). As disclosed herein, a peptide sequence containing as few as four amino acid residues can be used as a linker between a dye residue and nucleobase in nucleoside triphosphates and can be cleaved efficiently by subtilisin A, chymotrypsin, or proteinase K proteases (see Examples). The peptide linked nucleosides can also be incorporated by polymerases.

Exemplary peptide linker dNTPs are shown in FIG. 2B. FIG. 2 shows the scheme for sequencing by synthesis (SBS) using nucleotides with enzymatically cleavable linkers. A schematic drawing of an SBS method is shown in FIG. 2A. FIG. 2B shows a proposed structure of a nucleotide having an enzymatically cleavable linker. The nucleotide contains a removable group at the 3' position and the dye linked to the nucleotide via a peptide that is cleavable by a protease. However, as disclosed herein, the removable group can be placed at the 2' or 4' position to generate a 2' or 4' reversible terminator, if desired. In order to demonstrate the concept, 10 of the best peptides are selected from over 1000 protease peptide substrates, and these peptides can be cleaved efficiently by very inexpensive commercial protease enzymes, such as subtilisin A, chymotrypsin, or proteinase K proteases (see Example III and FIG. 3). A sequencing method can also be performed with nucleotides having a peptide linker but without a blocking group, as disclosed herein.

As disclosed herein, among the 10 peptide sequences, one peptide was selected for further optimization to reduce peptide length (see Example III). One model peptide containing 4 amino acids is selected to link the nucleoside and a fifth amino acid residue to which a dye molecule is attached (see Example III and FIG. 4).

Figure 6:
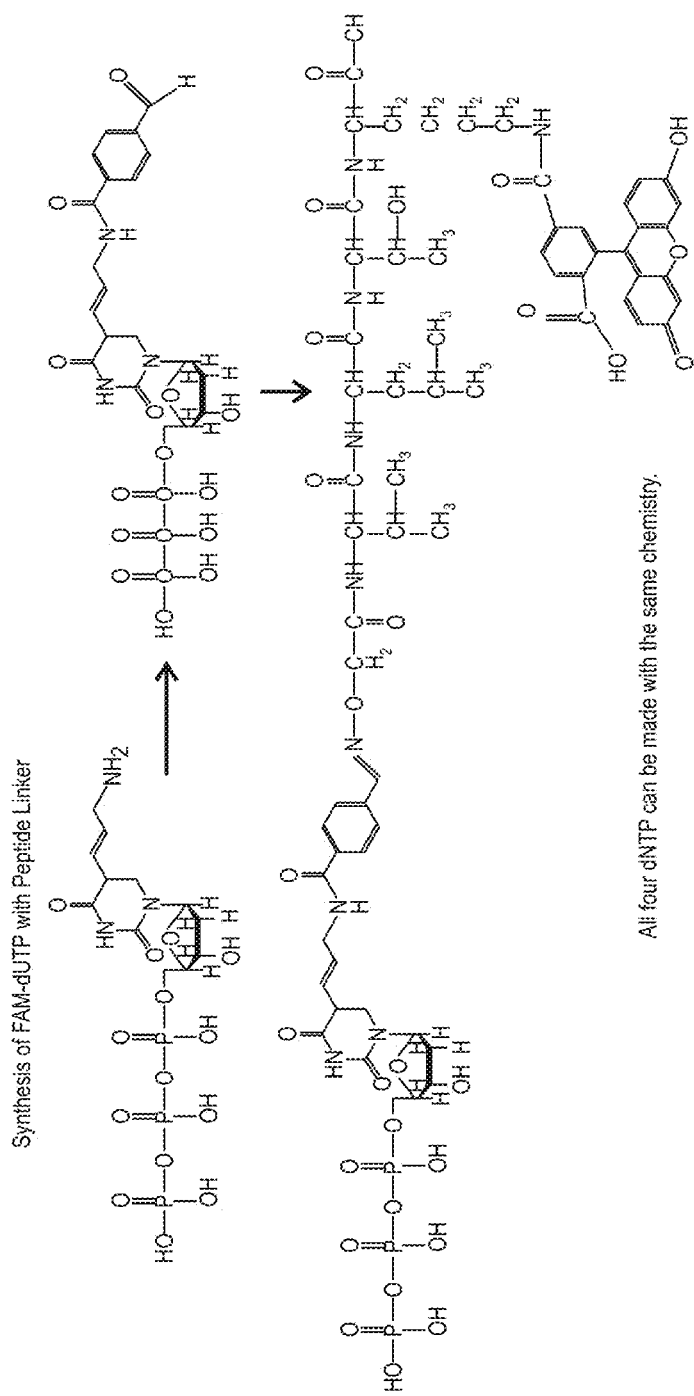
FIG. 6 shows a scheme for the synthesis of FAM-dUTP with a peptide linker.
Figure 7:
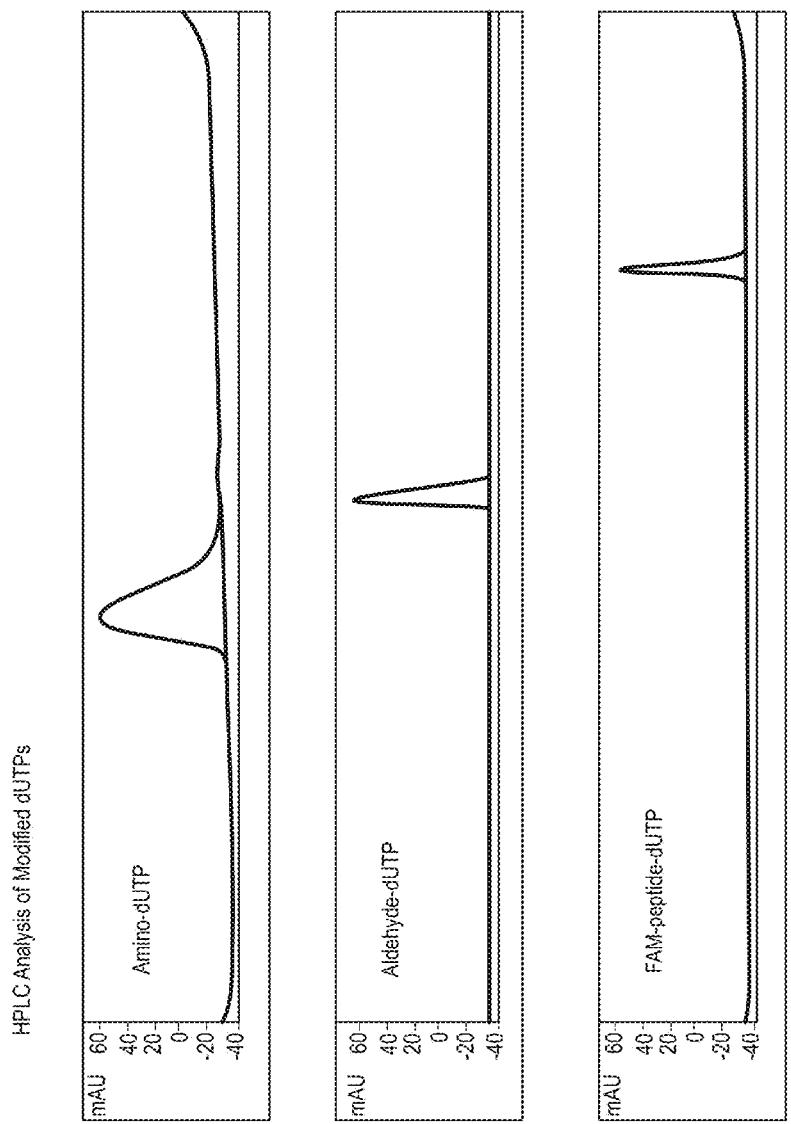
FIG. 7 shows HPLC analysis of modified dUTPs, amino-dUTP, aldehyde-dUTP and FAM-peptide-dUTP.

Example IV and FIG. 6 show one example of synthesizing peptide linked dNTPs. FIG. 7 shows the HPLC profiles of aldehyde modified dUTP and FAM-labeled peptide linked dUTP.

The FAM-labeled peptide linked dUTP was tested based on incorporation using commercially available polymerase in both solution and on BeadArray™ (see Example IV and FIGS. 8 and 9). The results disclosed herein show that 1) the peptide linked dUTP can be incorporated onto primers with specificity; and 2) after the incorporation, the dye molecule can be removed by enzymatic peptide cleavage.

Figure 10:
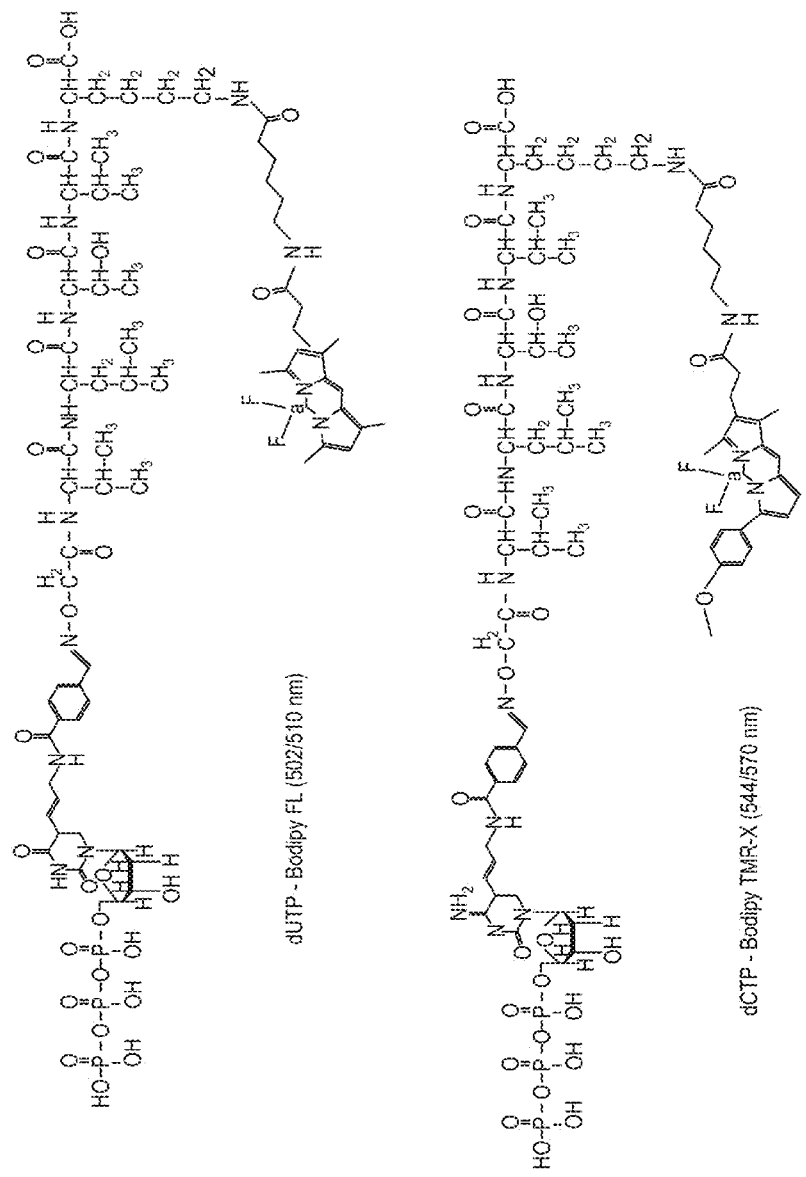
FIG. 10 shows four dNTPs with different Bodipy dye molecules.
Figure 10:
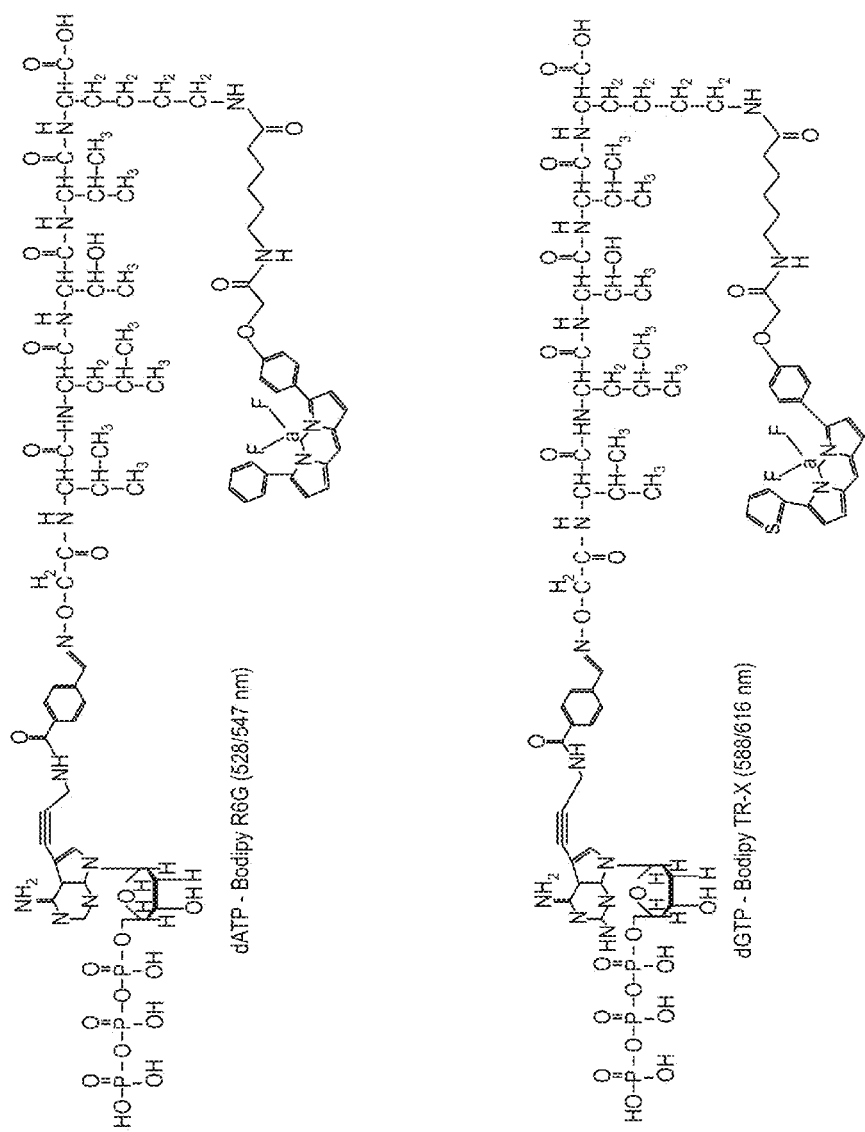
Figure 11:
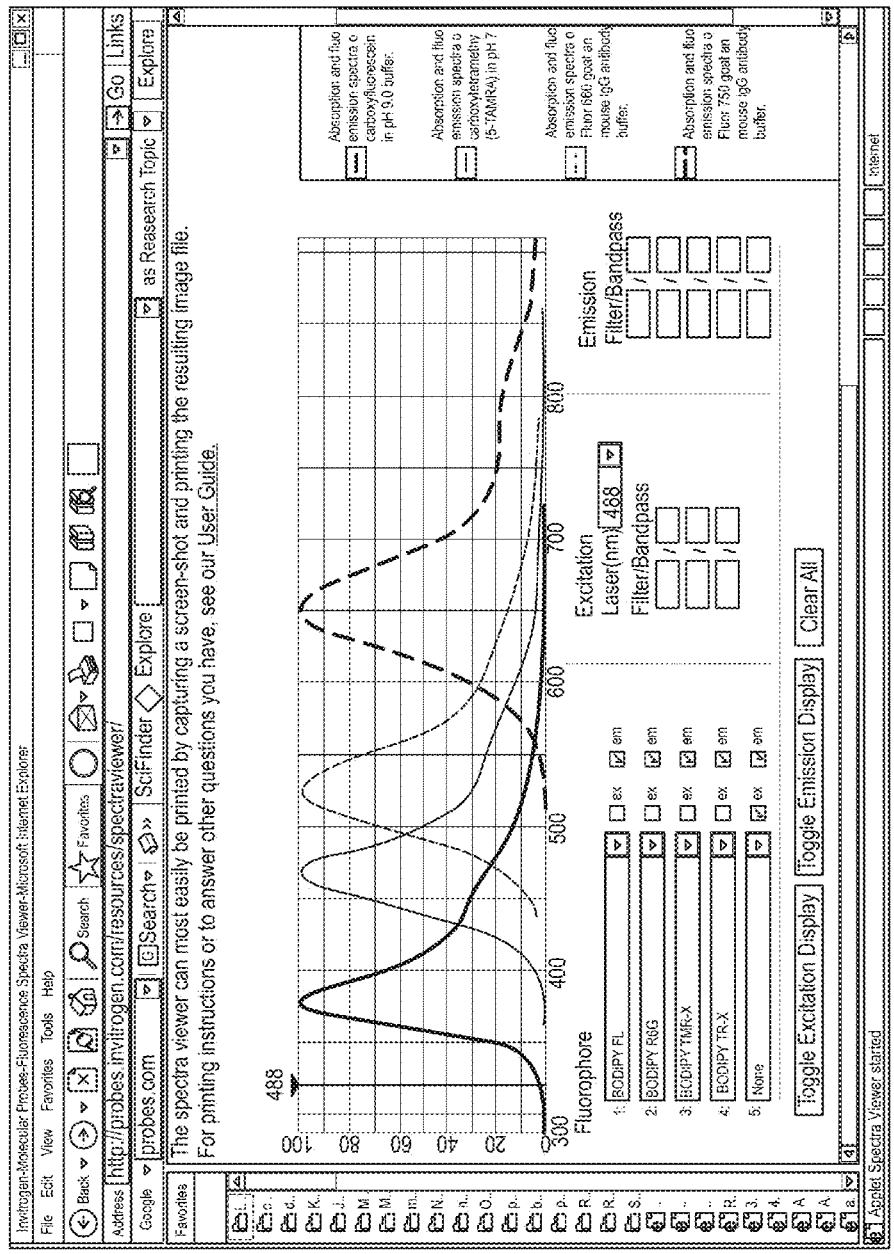
FIG. 11 shows emission spectra for the Bodipy dye molecules shown in FIG. 10.
Figure 12:
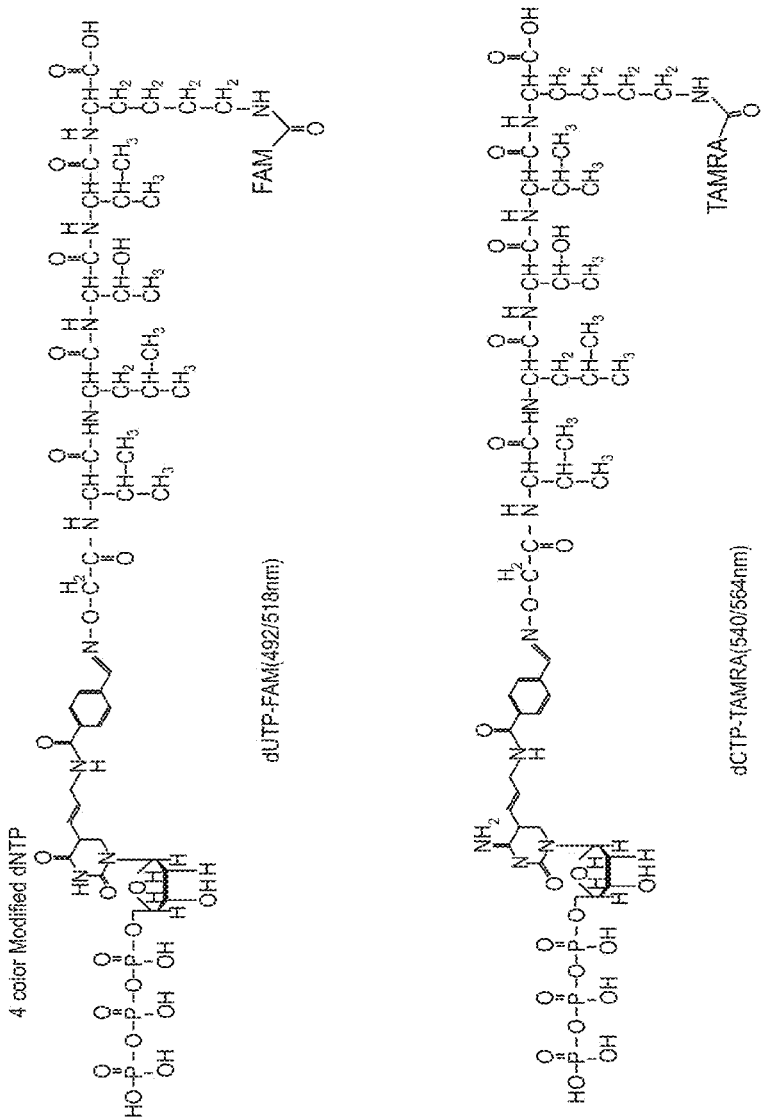
FIG. 12 shows four dNTPs with a different dyes, FAM, TAMRA, $Alexa_{660}$ and $Alexa_{750}$.
Figure 12:
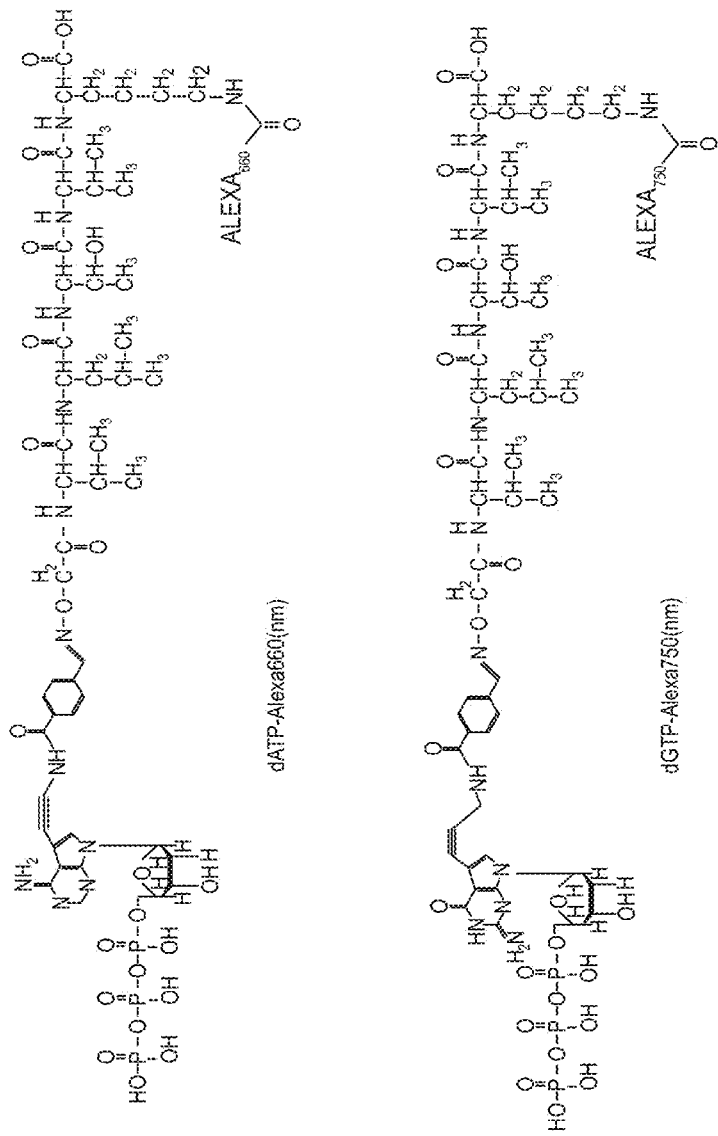
Figure 13:
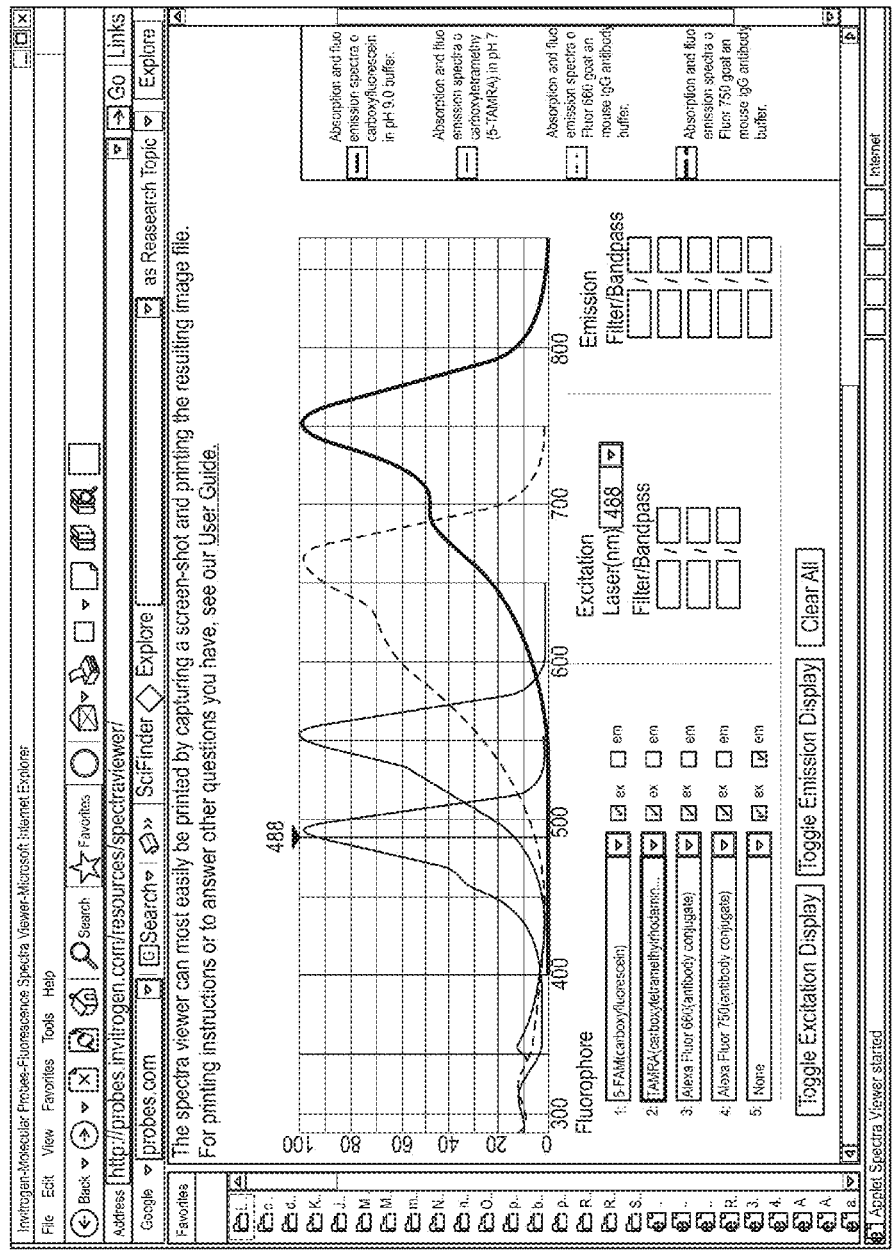
FIG. 13 shows emission spectra for the dyes shown in FIG. 12.

As disclosed herein, a variety of fluorophores can be linked to a cleavable peptide linker (see Example IV). Through the peptide linker, different nucleosides can be attached to different dye molecules. FIGS. 10 and 11 show 4-color Bodipy dyes attached dNTPs and their possible emission spectra. FIGS. 12 and 13 show a different set of 4-color dNTPs and their emission spectra.

One aspect of the present invention relates to the recognition that an aqueous enzymatic cleavage method of removing dye molecules would be much more compatible with primer/DNA hybridization conditions than many existing methods, for example, those using high temperature cleavable linkers. Also, the methods can be carried out without the need for additional expensive equipment, for example, high powered lasers which are typically used for photo-cleavage of photo-cleavable linkers.

In one embodiment, the invention provides a nucleoside or nucleotide molecule, comprising a label linked to the molecule by an enzymatically cleavable peptide linker. The label can be linked, for example, to the base of nucleoside or nucleotide molecule.

As used herein, a "nucleoside" refers to a nucleic acid component that comprises a base or basic group, for example, comprising at least one homocyclic ring, at least one heterocyclic ring, at least one aryl group, and/or the like, covalently linked to a sugar moiety such as a ribose sugar, a derivative of a sugar moiety, or a functional equivalent of a sugar moiety, for example, an analog, such as carbocyclic ring. For example, when a nucleoside includes a sugar moiety, the base is typically linked to a 1'-position of that sugar moiety. A base can be naturally occurring, for example, a purine base, such as adenine (A) or guanine (G), a pyrimidine base, such as thymine (T), cytosine (C), or uracil (U)), or can be non-naturally occurring, for example, a 7-deazapurine base, a pyrazolo[3,4-d]pyrimidine base, a propynyl-dN base, or other analogs or derivatives as disclosed herein or are well known in the art. Exemplary nucleosides include ribonucleosides, deoxyribonucleosides, dideoxyribonucleosides, carbocyclic nucleosides, and the like. Other examples of nucleotides include those having analog structures set forth herein in regard to oligonucleotide primers.

A "nucleotide" refers to an ester of a nucleoside, for example, a phosphate ester of a nucleoside. For example, a nucleotide can include 1, 2, 3, or more phosphate groups covalently linked to a 5' position of a sugar moiety of the nucleoside. As used herein, an "extendible nucleotide" refers to a nucleotide to which at least one other nucleotide can be added or covalently bonded, for example, in a reaction catalyzed by a nucleotide incorporating catalyst once the extendible nucleotide is incorporated into a nucleotide polymer. Examples of extendible nucleotides include deoxyribonucleotides and ribonucleotides. An extendible nucleotide is typically extended by adding another nucleotide at a 3'-position of the sugar moiety of the extendible nucleotide. A nucleotide can be a triphosphate form (NTP) such, as a deoxyribonucleotide triphosphate (dNTP), dideoxyribonucleotide triphosphate (ddNTP) or ribonucleotide triphosphate (rNTP). Other examples of nucleotides include those having analog structures set forth herein in regard to oligonucleotide primers.

In another embodiment, the nucleoside or nucleotide molecule can further comprise a blocking group. As used herein, a "blocking group" refers to a chemical group which, when attached to a nucleotide, inhibits further extension of a nucleic acid when the nucleotide is incorporated into the nucleic acid. The chemical group can inhibit extension by a nucleotide incorporating catalyst such as a polymerase, ligase, terminal transferase, reverse transcriptase, polynucleotide phosphorylase, telomerase, or the like. Typically, the blocking group prevents attachment of the 3' hydroxyl to the 5' phosphate of another nucleotide. The presence of such a blocking group in a nucleotide can be referred to herein as a "terminator" since the extension reaction by the nucleotide incorporating catalyst is inhibited, that is, terminated. A terminator can also be referred to herein as a "non-extendible" nucleotide since, upon incorporation into a nucleic acid, it prevents further extension of the nucleic acid, for example, by at least one nucleotide incorporating catalyst.

As disclosed herein, a blocking group can be removable. As used herein, a "removable" blocking group refers to a chemical group that can be removed item the nucleotide such that a nucleotide incorporating catalyst can extend the nucleic acid by the incorporation of at least one additional nucleotide, examples of which include an extendible nucleotide or a non-extendable nucleotide such as a terminator containing either a removable or non-removable blocking group. Such a blocking group can therefore be removed from the terminator incorporated into a nucleic acid such, that the nucleic acid containing the terminator remains intact other than the removal of the blocking group. A nucleotide containing a removable blocking group is also referred to herein as a "reversible terminator." Thus, in order for the nucleic acid to become extendible, the reversible terminator would remain linked to the nucleic acid through a phosphate bond or other bond that links the nucleotides of the nucleic acid and reveals a group such as an hydroxyl group to which another nucleotide can be added to extend the nucleic acid. Such conditions can include enzymatic or chemical cleavage. Particularly useful conditions for removing a blocking group include those under which a nucleic acid can remain hybridized to an at least partially complementary nucleic acid sequence. It is understood that removal of a blocking group can leave an hydroxyl or other chemical moiety at the position where the blocking group was attached. Thus, removal of blocking group does not require that all of the blocking group be removed, only that a sufficient portion of the blocking group be removed such that a nucleotide incorporating catalyst can extend the nucleic acid by the incorporation of at least one additional nucleotide.

Exemplary removable blocking groups are described herein. Such removable blocking groups include, but are not limited to, those shown in FIG. 1A. For example, a sulfate group can also be used as a blocking group. Blocking groups include, but are not limited to, allyl, acetal, aminal and thial groups. Additional removable blocking groups have been described in WO 91/06678, which is incorporated herein by reference. Blocking groups are also described, for example, in WO 2005/005667, which is incorporated herein by reference.

Methods for synthesizing nucleosides or nucleotides containing a blocking group are well known to those skilled in the art and are described herein (see Example I). Synthesis of nucleosides or nucleotides containing blocking groups have also been, described, for example, in WO91/06678; U.S. publication 2005/037991; WO 2005/005667; WO 2004/018497; U.S. Pat. No. 7,057,026; Metzker et al., *Nucl. Acids Res.* 22:4259-4267 (1994); Canard and Sarfati, *Gene* 148:1-6 (1994); Meng et al., *J. Org. Chem.* 14:3248-3252 (2006); Lu and Burgess, *Bioorgan. Med. Chem. Lett.* 16:3902-3905 (2006), each of which is incorporated herein by reference. Exemplary blocking groups and conditions for removing the blocking groups are listed in Table 1.

TABLE 1

Exemplary Blocking Groups[1].

| Blocking Group | Reference | Removal Conditions |
|---|---|---|
| —$CH_2$—CH=$CH_2$ | WO 91/06678 | Pd, heat |
| —$CH_2$—$N_3$ | WO 2004/018497 | water-soluble phosphine |
| —$CH_2$—S—S-tBu | | DTT |
| —$CH_2$—S—Me | | acid |
| —$CH_2$—O—$CH_2$—$CH_2$—CN | | 1M TBAF/THF |
| —$CH_2$—$CH_2$—CN | | 1M TBAF/THF |
| —C(O)—$CH_3$ | Metzker 1994, WO 91/06678 | lipase |

TABLE 1-continued

Exemplary Blocking Groups[1].

| Blocking Group | Reference | Removal Conditions |
|---|---|---|
| —$CH_3$ | Metzker 1994, WO 91/06678 | |
| 2-nitrobenzyl | Metzker 1994 | |
| tetrahdyropyran | Metzker 1994 | acid |
| 4-nitrobenzoyl | Metzker 1994 | |
| 2-aminobenzoyl | Metzker 1994, Canard 1994 | 0.1M NaOH, proteinase K |
| —C(O)-linker-dye | Canard 1994, WO 91/06678 | 0.1M NaOH proteinase K |
| 2-nitrobenzyl-linker-dye | Burgess 2006 | light |
| —C(O)—O—$CH_2$—CH=CH-linker-dye | Burgess 2006 | Pd, heat |
| —NH—C(O)—$CH_3$ | WO 91/06678 | Penicillin G acylase |
| —F | WO 91/06678 | |
| —$NH_2$ | WO 91/06678 | |
| Phosphate | WO 91/06678 | phosphatase |
| Sulfate | | sulfatase |

[1]Abbreviations: Ph, phenyl; Bu, butyl; DTT, dithiothreitol; TBAF, tetra-n-butylammonium fluoride; THF, tetrahydrofuran;

Additional exemplary removable blocking groups have been described in WO 91/06678, which is incorporated herein by reference. Although, generally described therein as 3' blocking groups, it is understood, as disclosed herein, that such blocking groups can be used on 2', 3' or 4' positions, as desired. Particularly useful blocking groups are esters and ethers. Other blocking groups include, for example, —F, —$NH_2$, —$OCH_3$, —$N_3$, —$OPO_3$", —$NHCOCH_3$, 2-nitrobenzene carbonate, 2,4-dinitrobenzene sulfenyl and tetrahydrofuranyl ether. As described in WO 91/06678, incorporation and chain termination have been demonstrated with many of these blocking groups (Kraveskii et al., *Molecular Biology* 21:25-29 (1987), which is incorporated herein by reference).

Particularly useful blocking groups are esters such as lower (1-4 carbon) alkanoic acid and substituted lower alkanoic acid esters, for example formyl, acetyl, isopropanoyl, alpha fluoro- and alpha chloroacetyl esters and the like; ether blocking groups such as alkyl ethers; phosphate blocking groups; carbonate blocking groups such as 2-nitrobenzyl; 2, 4-dinitrobenzene-sulfenyl and tetrahydrothiofuranyl ether blocking groups. Blocking groups can be modified to incorporate reporter moieties, if desired, including radiolabels (tritium, $C^{14}$ or $P^{32}$, for example), enzymes, fluorophores and chromophores, if desired. In addition enzymes can be used to remove ester linked groups. For example phosphate groups can be removed with a phosphatase and acetyl groups can be removed with esterases.

As described in WO 91/06678, esters and phosphate, can be incorporated into nucleosides or nucleotides, as described below. For example, 5'-dimethoxytrityl (DMT) thymidine can be prepared from thymidine by reaction with DMT chloride in pyridine, followed by acetylation of the 3'-OH function using acetic anhydride in pyridine (Zhdanov and Zhenodarova, *Synthesis* 1975:222-245 (1975), which is incorporated herein by reference). The 5'-DMT group is treated with 2% benzene-sulfonic acid and converted into the phosphomonoester by reaction with $POCl_3$ in trimethyl phosphate (Papchikhin et al., *Bioorganic Chemistry* 11:716-727(1985), which is incorporated herein by reference) and by purification using chromatography. The 5'-monophosphate is converted into the 5'-triphosphate by activation with N, N'-carbonyldiimidazole, followed by pyrophosphorylation with tri(n-butylammonium) pyrophosphate (Papchikhin et al., supra, 1985) and purification by chromatography.

Preparation of —O-acetyl derivatives of ATP, CTP, and GTP follows the same general scheme, with additional steps to protect and deprotect the primary amino functions. Because 5'-triphosphate derivatives of nucleosides are often unstable, the final preparative steps outlined above can be optionally carried out just before introducing the nucleoside or nucleotide into the reaction vessel. If radiolabeled acetic anhydride is used, this serves to introduce a label into the ester blocking group.

When carrying out ester-blocking of an hydroxyl group, the primary amino residues in cytosine, adenine, and guanine are also susceptible to attack by electrophilic reagents such as acetic anhydride and can be advantageously protected. In chemical oligonucleotide synthesis (phosphotriester phosphoramidite approaches), various N-acyl groups are commonly used for protection of the primary amine (Papchikhin et al., supra, 1985). Because the N-acyls are stable in acidic and neutral solutions, removal is typically effected by ammonolysis. These conditions are likely to cleave 3'-O-acyl blocking groups and other blocking groups hydrolyzable under basic conditions, so alternative protection can be used if it is desired to selectively remove the amino group protection. Several selectively-removable amine protection groups include carbamates cleavable by acid hydrolysis (t-butyl, 2-(biphenyl) isopropyl) and certain amides susceptible to acid cleavage (formamide, trichloroacetamide) (Greene *Protective Groups in Organic Synthesis*, John Wiley and Sons, Inc., New York, N.Y. (1981), which is incorporated herein by reference).

As described in WO 91/06678, monophosphate blocking groups on NTPs can be synthesized by a modification of procedures for chemical oligonucleotide synthesis using the H-phosphonate method (Froehler et al., *Nucleic Acids Research* 14:5399-5407 (1986), which is incorporated herein by reference). 5'-DMT-3'-thymidine H-phosphonate can be prepared by reaction of 5'-DMT thymidine with phosphorous trichloride, 1, 2, 4-triazole, and N-methylmorpholine. Removal of the 5'-protecting group and formation of the 5'-triphosphate moiety can be performed as described in WO 91/06678. The phosphonate is converted to the monophosphate by oxidation with iodine in basic solution.

For other nucleotide derivatives, protection of the primary amino groups is performed prior to phosphonation. In this preparation, standard amino protecting groups cleavable by ammonolysis can be used.

Deblocking methods are also described in WO 91/06678. For example, removal of ester blocking groups can be achieved by base hydrolysis. Generally, the greater the electro-negativity of substituents on the carbonyl carbon, the greater the ease of removal. For example, the highly electronegative group trifluoroacetate can be cleaved rapidly from 3' hydroxyls in methanol at pH 7 and thus would not be stable during coupling at that pH. Phenoxyacetate groups are cleaved in less than one minute but require substantially higher pH such as is achieved with $NH_3$/methanol (Reese and Steward, *Tetrahedron Letters* 40:4273-4276 (1968), which is incorporated herein by reference). To prevent significant premature deblocking and nucleic acid degradation, the ester deblocking rate can be advantageously selected so as to exhibit a different deblocking rate during the incorporation than during the deblocking stage. This rate change can be achieved, for example, by changing the buffer pH from 7 to about 10.

A wide variety of hydroxyl blocking groups are cleaved selectively using chemical procedures other than base hydrolysis. 2,4-Dinitrobenzenesulfenyl groups can be cleaved rapidly by treatment with nucleophiles such as thiophenol and thiosulfate (Letsinger et al., *J. Organic Chemistry* 29:2615-2618 (1964), which is incorporated herein by reference). Allyl ethers can be cleaved by treatment with Hg(II) in acetone/water (Gigg and Warren, *J. Chemical Society* C14:1903-1911 (1968), which is incorporated herein by reference). Tetrahydrothiofuranyl ethers can be removed under neutral conditions using Ag(I) or Hg(II) (Cohen and Steele, *J. Organic Chemistry* 31:2333(1966); Cruse et al., *J. Organic Chemistry* 43:3548-3553 (1978), each of which is incorporated herein by reference). These protecting groups, which are stable to the conditions used in the synthesis of NTP analogues and in the sequence incorporation steps, have some advantages over groups cleavable by base hydrolysis because deblocking occurs only when the specific deblocking reagent is present and premature deblocking during incorporation is minimized.

Photochemical deblocking can be used with photochemically-cleavable blocking groups. Several blocking groups are available for such an approach. As described in WO 91/06678, the use o-nitrobenzylethers as protecting groups for 2'-hydroxyl functions of ribonucleosides is known (Ohtsuka et al., *J. American Chemical Society* 100:8210-8213 (1978), which is incorporated herein by reference); removal occurs by irradiation at 260 nm. Alkyl o-nitrobenzyl carbonate protecting groups are also cleaved by irradiation at pH 7 (Cama and Christensen, *J. American Chemical Society* 100:8006 (1978), which is incorporated herein by reference).

Enzymatic deblocking of blocking groups is also possible. As described in WO 91/06678, it has been demonstrated that T4 polynucleotide kinase can convert 3'-phosphate termini to 3'-hydroxyl termini that can then serve as primers for DNA polymerase I (Henner et al., *J. Biological Chemistry* 258:151198-15205 (1983), which is incorporated herein by reference). Other enzymatic methods for removal of blocking groups are described herein.

As described in WO 91/06678, additional modifications can be included to improve the efficiency and speed of each step. Upon selection, of the optimal methodology for incorporation and deblocking, other nonchemical assistance can be used to accelerate chemical deblocking. These methods include, for example, applying controlled ultrasonic irradiation of the reaction chamber to increase the rate of the deblocking step if mass transport limitations are significant and raising the reaction temperature up to about 50° C. for a short period.

It is understood that any of a variety of suitable conditions can be used to remove a blocking group, including enzymatic, chemical or photolytic removal. Enzymatic removal is particularly useful when using a peptide linker that is cleavable by a protease since the enzymatic removal of the label by cleavage of the peptide linker and removal of the blocking group can be carried out sequentially or simultaneously in aqueous solution. Conditions for chemically removing a blocking group are carried out under conditions that permit subsequent steps to be performed. For example, the chemistry would either not affect other chemical groups on the nucleoside or nucleotide or incorporate blocking groups that prevent modification of other groups during the deblocking reaction. If the reaction is a sequencing by synthesis method involving a hybridization reaction, it is particularly useful if the deblocking steps are performed such that the extending nucleic acid remains hybridized to its template nucleic acid.

The blocking group can be attached at the 2', 3' or 4' position of the sugar moiety of the nucleoside or nucleotide molecule, in particular on a ribose sugar of the nucleoside or nucleotide. Exemplary removable blocking groups include, but are not limited to those shown in FIG. 1A.

The label on such a nucleoside or nucleotide molecule cast be a ligand or dye, including, for example, a fluorescent dye such as FAM, Bodipy, TAMRA or Alexa. Other exemplary label and dye molecules are disclosed herein.

As disclosed herein, a linker can be cleaved by a protease (see Examples III and IV). Exemplary proteases include, but are not limited to, proteinase K, trypsin, chymotrypsin, subtilisin or V8 protease, or other proteases disclosed herein.

In another embodiment, the invention provides a nucleoside or nucleotide molecule comprising a removable blocking group at the 2' or 4° position of the sugar moiety of the molecule, with the proviso that the removable blocking group is not a phosphate group at the 2' position. Exemplary removable blocking groups include those shown in FIG. 1A. Such a molecule can further contain a label such as a dye, for example, a fluorescent dye, or a ligand. However, a nucleoside or nucleotide having a removable blocking group need not include a label.

The compositions of the invention are particularly useful for sequencing nucleic acid molecules, in particular nucleoside triphosphates that contain removable blocking group. Such nucleoside triphosphates are referred to herein as reversible terminator-nucleoside triphosphates.

In another embodiment, the invention provides a method for sequencing a nucleic acid molecule. The method can include the steps of incubating a nucleic acid molecule with a polymerase in the presence of a reversible terminator nucleoside triphosphate (RT-NTP) comprising a removable blocking group and a label linked to the RT-NTP by an enzymatically cleavable peptide linker, wherein a primer is extended to incorporate the RT-NTP into a sequence complementary to the nucleic acid molecule; and identifying the RT-NTP in the complementary sequence, wherein identifying the RT-NTP identifies at least a portion of the sequence of the nucleic acid molecule. Such a method can further include the step of removing the removable blocking group from the RT-NTP in the sequence complementary to the nucleic acid molecule. In addition, such a method can further include cleaving the cleavable linker to remove the label from the RT-NTP in the sequence complementary to the nucleic acid molecule. If desired, the removing and cleaving steps can be carried out in the same reaction. This is particularly useful when both the removing and cleaving steps are carried out enzymatically and the enzymes are active in the same buffer conditions.

In a method for sequencing a nucleic acid molecule, a second RT-NTP can be added and incubated as described herein, where the complementary sequence is extended and the second RT-NTP is incorporated into the sequence complementary to the nucleic acid molecule. Thus, a second round of incorporation of an RT-NTP can be performed. Additionally, the second RT-NTP can be identified, for example, by detecting a label such as a ligand or dye, such that at least a portion of the sequence of the nucleic acid molecule is identified. Similarly, the removing and cleaving steps can be repeated. If desired, the steps of incubating, identifying, removing and cleaving can be repeated any number of desired times such that at least a portion of the sequence of the nucleic acid molecule is determined.

The compositions and methods of the invention can be used in a sequencing by synthesis method such that a desired length of sequence information can be determined for a target nucleic acid molecule. In one embodiment, two or more different RT-NTPs are added to the incubation reaction, where each of the different RT-NTPs comprises a different base and a different label. In a particularly useful embodiment, four different RT-NTPs are added, where a different label is associated with each of four different bases. By having a different label associated with each of the four bases (see Example IV), each of the bases can be readily identified, including if added together. For example, the label can be a dye, for example, a fluorescent dye. Exemplary fluorescent dyes include FAM, Bodipy, TAMRA and Alexa, and others as disclosed herein.

In a particular embodiment, the removable blocking group can be removed by incubation with a phosphatase, for example, a phosphate blocking group (see Example II). Blocking groups can be removed enzymatically, chemically or photolytically, as disclosed herein.

In the case of a nucleoside or nucleotide containing a label linked by an enzymatically cleavable linker, the label can be removed by cleavage of the cleavable linker with a protease. In particular, a protease can be conveniently used with a peptide linker containing a protease cleavage site, as disclosed herein.

In yet another embodiment, the invention provides a method for sequencing a nucleic acid molecule. Such a method can include the steps of incubating a nucleic acid molecule with a polymerase in the presence of a nucleoside triphosphate (NTP) comprising a label linked to the NTP by an enzymatically cleavable peptide linker, wherein a primer is extended to incorporate the NTP into a sequence complementary to the nucleic acid molecule; and identifying the NTP in the complementary sequence, wherein identifying the NTP identifies at least a portion of the sequence of the nucleic acid molecule. Such a method can further include the step of cleaving the cleavable linker to remove the label from the NTP in the sequence complementary to the nucleic acid molecule.

In a method of sequencing a nucleic acid molecule a second NTP comprising a label linked to the NTP by an enzymatically cleavable peptide linker can be added and the incubation step repeated, wherein the complementary sequence is extended and the second NTP is incorporated into the sequence complementary to the nucleic acid molecule. Similarly, the identification step can be repeated, wherein identifying the second NTP identifies at least a portion of the sequence of the nucleic acid molecule. In addition, the cleaving step can be repeated such that the label from the second NTP is removed. Furthermore, the incubating, identifying and cleaving steps can be repeated a desired number of times such that at least a portion of the sequence of the nucleic acid molecule is determined. If desired in a sequencing method, four different NTPs can be added, wherein a different label is associated with each of four different bases.

If desired, the label can be removed by cleavage of the cleavable linker with a protease, in particular a peptide linker. As disclosed herein, any of a number of peptide linkers and corresponding proteases can be used.

In a particular embodiment, the label can be a ligand or dye, for example, a fluorescent dye. Exemplary fluorescent dyes include a fluorophore selected from FAM, Bodipy, TAMRA and Alexa, as well as other dyes disclosed herein.

In still another embodiment, the invention provides a method for sequencing a nucleic acid molecule. The method can include the steps of incubating a nucleic acid molecule with a polymerase in the presence of an RT-NTP comprising a removable blocking group at the 2' or 4' position of the sugar moiety of the molecule, wherein a primer is extended to incorporate the RT-NTP into a sequence complementary to the nucleic acid molecule; and identifying the RT-NTP in the complementary sequence, wherein identifying the RT-NTP identifies at least a portion of the sequence of the nucleic acid molecule. Such a method of sequencing a nucleic acid molecule can further include the step of removing the removable blocking group from the RT-NTP in the sequence complementary to the nucleic acid molecule.

A method of sequencing a nucleic acid molecule can further include adding a second RT-NTP and repeating the incubation step, wherein the complementary sequence is extended and the second RT-NTP is incorporated into the sequence complementary to the nucleic acid molecule. Such a method can further include repeating the identifying step, wherein identifying the second RT-NTP identifies at least a portion of the sequence of the nucleic acid molecule. The method can further include repeating the removing step such that the complementary sequence can be further extended. The steps of adding RT-NTPs and repeating the incubating, identifying and removing steps can be performed one or more times, or any desired number of times, such that at least a portion of the sequence of the nucleic acid molecule is determined. If desired, two or more different RT-NTPs can be added to the incubation reaction, where each of the different RT-NTPs contains a different base and a different dye. In a particularly useful embodiment, four different RT-NTPs can be added, where a different dye is associated with each of the four different bases.

The removable blocking group can be removed by incubation with a phosphatase, in particular when the blocking group is a phosphate group. As disclosed herein, any of a number of methods for removing a blocking group can be employed, including enzymatic, chemical and photolytic, depending on the type of blocking group.

In embodiments where the sequence of a nucleic acid molecule is to be determined, cycles, such as those exemplified above and elsewhere herein can be repeated. Each cycle can include any number of steps for determining the identity of a nucleotide at a particular sequence location. For example, in embodiments utilizing nucleotides having a reversible blocking group and an enzymatically cleavable label each cycle can include the steps of adding such a nucleotide to a primer, detecting the label on the primer, removing the label and removing the blocking group. Optionally, steps of removing a label or removing a blocking group can be omitted, for example, when the nucleotides used do not include a removable label or removable blocking group, respectively. Cycles can be repeated to determine a sequence present in a template to which the primer is hybridized. The number of cycles performed in a sequencing method can be at least 10, 25, 50, 75, 100, 150, 200, 250 or more. Cycles can be repeated until a predetermined length of sequence has been determined including, for example, until a sequence length of at most 25, 50, 75, 100, 150, 200, 250 or 500 nucleotides has been determined. The above-described ranges are merely exemplary and are not intended to limit the use of the methods. It will be understood that any number of cycles can be performed as desired, for example, within a perceived or accepted limit of detection for the embodiment employed.

Another embodiment of the invention provides a method for extending a primer nucleic acid. The method can include the steps of incubating a template nucleic acid molecule with a nucleotide incorporating catalyst, a primer nucleic acid molecule and a nucleotide molecule comprising a label linked to the nucleotide molecule by an enzymatically cleavable peptide linker, whereby the catalyst extends the primer nucleic acid to produce an extended primer nucleic acid molecule incorporating the nucleotide molecule.

In a method for extending a primer nucleic acid, the nucleotide molecule can further contain a blocking group, for example, a removable blocking group. The blocking group can be enzymatically removable. The method can further include the step of removing the label and the blocking group from the nucleotide using enzymes. In a particular embodiment, the label and the blocking group can be removed using different enzymes contacted with the nucleotide in the same or a sequential reaction.

A nucleotide incorporating catalyst can be selected, for example, from a polymerase, a terminal transferase, a reverse transcriptase, a polynucleotide phosphorylase and a telomerase. A method for extending a primer nucleic acid can further include the step of incubating with one or more extendible nucleotides. The blocking group is generally attached at the 2', 3' or 4' position of the sugar moiety of the molecule. A removable blocking group can be selected, for example, from those shown in FIG. 1A or others disclosed herein or well known in the art.

In one embodiment of a method for extending a primer nucleic acid, the nucleotide molecule can contain a label. The label can be, for example, a ligand or a dye. For example, the dye can be a fluorescent dye such as a fluorophore selected from FAM, Bodipy, TAMRA and Alexa or others as disclosed herein. The linker, in particular a peptide linker, can be cleaved by a protease. The protease can be, for example, proteinase K, trypsin, chymotrypsin, subtilisin and V8 protease, or other proteases as disclosed herein and well known in the art.

In yet another embodiment, the invention provides a method of ligating two nucleic acid molecules by incubating first and second nucleic acid molecules in the presence of a ligase, wherein at least one of the first and second nucleic acid molecules comprises on the 3' end a nucleoside comprising a removable blocking group. The removable blocking group is generally attached at the 2', 3' or 4' position of the sugar moiety of the nucleoside comprising a removable blocking group. The nucleoside comprising a removable blocking group can further comprise a label linked by an enzymatically cleavable peptide linker.

In a method of ligating two nucleic acid molecules, the nucleotide molecule can further contain a blocking group, for example, a removable blocking group. The blocking group can be enzymatically removable. The method can further include the step, of removing the label and the blocking group from the nucleotide using enzymes. In a particular embodiment, the label and the blocking group can be removed using different enzymes contacted with the nucleotide in the same or a sequential reaction.

In a method of ligating two nucleic acid molecules, a label can be linked to the base of the nucleoside containing a blocking group. The blocking group is generally attached at the 2', 3' or 4' position of the sugar moiety of die nucleoside containing a blocking group. The removable blocking group can be selected from those shown in FIG. 1A or other removable blocking groups, as disclosed herein.

The label on the nucleoside can be a ligand or dye, for example, a fluorescent dye. The fluorescent dye can be a fluorophore selected from FAM, Bodipy, TAMRA and Alexa or others, as disclosed herein.

The linker on the nucleoside can be cleaved by a protease, particularly a peptide linker. The protease can be selected from proteinase K, trypsin, chymotrypsin, subtilisin and V8 protease, or others, as disclosed herein.

A nucleic acid sample that is amplified, sequenced or otherwise manipulated in a method disclosed herein can be, for example, DNA or RNA. Exemplary DNA species include, but are not limited to, genomic DNA (gDNA), mitochondrial DNA, and copy DNA (cDNA). One non-limiting example of a subset of genomic DNA is one particular chromosome or one region of a particular chromosome. Exemplary RNA species include, without limitation, messenger RNA (mRNA), transfer RNA (tRNA), or ribosomal RNA (rRNA). Further species of DNA or RNA include fragments or portions of the species listed above or amplified products derived from these species, fragments thereof or portions thereof. The methods described herein are applicable to the above species encompassing all or part of the complement present in a cell. For example, using methods described herein the sequence of a substantially complete genome can be determined or the sequence of a substantially complete mRNA or cDNA complement of a cell can be determined.

In general, an amplification method used in the invention can be carried out using at least one primer nucleic acid that hybridizes to a template nucleic acid to form a hybridization complex, nucleoside triphosphates (NTPs) and a polymerase which modifies the primer by reacting the NTPs with the 3' hydroxyl of the primer, thereby replicating at least a portion of the template. For example, PCR based methods generally utilize a DNA template, two primers, dNTPs and a DNA polymerase. A primer or NTP used in an amplification method can have a reversible blocking group on a 2', 3' or 4' hydroxyl, a peptide linked label or a combination thereof. Other amplification methods that can benefit from use of such a primer or NTP include those set forth elsewhere herein, for example, in the context of preparing templates for sequencing and other analytical methods.

A primer used in a method of the invention can have any of a variety of compositions or sizes, so long as it has the ability to hybridize to a template nucleic acid with sequence specificity and can participate in replication of the template. For example, a primer can be a nucleic acid having a native structure or an analog thereof. A nucleic acid with a native structure generally has a backbone containing phosphodiester bonds and can be, for example, deoxyribonucleic acid or ribonucleic acid. An analog structure can have an alternate backbone including, without limitation, phosphoramide (see, for example, Beaucage et al., *Tetrahedron* 49(10):1925 (1993) and references therein; Letsinger, *J. Org. Chem.*

35:3800 (1970); Sprinzl et al., *Eur. J. Biochem.* 81:579 (1977); Letsinger et al., *Nucl. Acids Res.* 14:3487 (1986); Sawai et al., *Chem. Lett.* 805 (1984), Letsinger et al., *J. Am. Chem. Soc.* 110:4470 (1988); and Pauwels et al., *Chemica Scripta* 26:141 91986)), phosphorothioate (see, for example, Mag et al., *Nucleic Acids Res.* 19:1437 (1991); and U.S. Pat. No. 5,644,048), phosphorodithioate (see, for example, Briu et al., *J. Am. Chem. Soc.* 11 1:2321 (1989), O-methyl-phophoroamidite linkages (see, for example, Eckstein, *Oligonucleotides and Analogues: A Practical Approach*, Oxford University Press), and peptide nucleic acid backbones and linkages (see, for example, Egholm, *J. Am. Chem. Soc.* 114:1895 (1992); Meier et al., *Chem. Int. Ed. Engl.* 31:1008 (1992); Nielsen, *Nature,* 365:566 (1993); Carlsson et al., *Nature* 380:207 (1996)). Other analog structures include those with positive backbones (see, for example, Denpey et al., *Proc. Natl. Acad. Sci. USA* 92:6097 (1995); non-ionic backbones (see, for example, U.S. Pat. Nos. 5,386,023, 5,637,684, 5,602,240, 5,216,141 and 4,469,863; Kiedrowski et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Left.* 4:395 (1994); Jeffs et al., *J. Biomolecular NMR* 34:17 (1994); *Tetrahedron Lett.* 37:743 (1996)) and non-ribose backbones, including, for example, those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook, Analog structures containing one or more carbocyclic sugars are also useful in the methods and are described, for example, in Jenkins et al., *Chem. Soc. Rev.* (1995) pp 169-176. Several other analog structures that are useful in the invention are described in Rawls, *C & E News* Jun. 2, 1997 page 35. The aforementioned analog structures can be included in a nucleoside or nucleotide that is further modified to include a reversible blocking group on a 2', 3' or 4' hydroxyl, a peptide linked label, or a combination thereof.

A further example of a nucleic acid with an analog structure that is useful in the invention is a peptide nucleic acid (PNA). The backbone of a PNA is substantially non-ionic under neutral conditions, in contrast to the highly charged phosphodiester backbone of naturally occurring nucleic acids. This provides two non-limiting advantages. First, the PNA backbone exhibits improved hybridization kinetics. Secondly, PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop in closer to 7-9° C. This can provide for better sequence discrimination. Similarly, due to their non-ionic nature, hybridization of the bases attached to these backbones is relatively insensitive to salt concentration. A PNA or monomer unit used to synthesize PNA can include a base having a peptide linked label. In such cases, an enzyme used to cleave the peptide linker will generally be unreactive toward the PNA backbone.

A nucleic acid useful in the invention can contain a non-natural sugar moiety in the backbone. Exemplary sugar modifications include but are not limited to 2' modifications such as addition of halogen, alkyl, substituted alkyl, SH, $SCH_3$, OCN, Cl, Br, CN, $CF_3$, $OCF_3$, $SO_2CH_3$, $OSO_2$, $SO_3$, $CH_3$, $ONO_2$, $NO_2$, $N_3$, $NH_2$, substituted silyl, and the like. Similar modifications can also be made at other positions on the sugar, particularly the 3' position of the sugar on the 3' terminal nucleotide or in 2'-5' linked oligonucleotides and the 5' position of 5' terminal nucleotide. Nucleic acids, nucleoside analogs or nucleotide analogs having sugar modifications can be further modified to include a reversible blocking group, peptide linked label or both. In those embodiments where the above-described 2' modifications are present, the base can have a peptide linked label.

A nucleic acid used in the invention can also include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid of the invention can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which basepairs with cytosine, adenine or uracil. Non-native bases can be modified to include a peptide linked label. The peptide can be attached to the base using methods exemplified herein with regard to native bases. Those skilled in the art will know or be able to determine appropriate methods for attaching peptides based on the reactivities of these bases. Alternatively or additionally, oligonucleotides, nucleotides or nucleosides including the above-described non-native bases can further include reversible blocking groups on the 2', 3' or 4' hydroxyl of the sugar moiety.

A nucleic acid having a modified or analog structure can be used, for example, to facilitate the addition of labels, analytical detection, or to increase the stability or half-life of the molecule under amplification conditions or other conditions used in accordance with the invention. As will be appreciated by those skilled in the art one or more of the above-described nucleic acids, nucleosides or nucleotides can be used for example, as a mixture including molecules with native or analog structures. In addition, a nucleic acid primer used in the invention can have a structure desired for a particular amplification technique or analytical method used in the invention, as desired. Exemplary analytical methods and amplification methods that can benefit from the nucleic acids, nucleosides or nucleotides of the invention are set forth below.

Nucleic acid sequencing has become an important technology with widespread applications, including mutation detection, whole genome sequencing, exon sequencing, mRNA or cDNA sequencing, alternate transcript profiling, rare variant detection, and clone counting, including digital gene expression (transcript counting) and rare variant detection. As disclosed herein, various amplification methods can be employed to generate larger quantities, particularly of limited nucleic acid samples, prior to sequencing.

Two useful approaches for high throughput or rapid sequencing are sequencing by synthesis (SBS) and sequencing by ligation. Target nucleic acid of interest can be amplified, for example, using ePCR, as per 454. Nucleic acid such as genomic DNA or others of interest can be fragmented, dispersed in water/oil emulsions and diluted such that a single nucleic acid fragment is separated from others in an emulsion droplet. A bead, for example, containing multiple copies of a primer, can be used and amplification carried out such that each emulsion droplet serves as a reaction vessel for amplifying multiple copies of a single nucleic acid fragment. Other methods can be used, such as bridging PCR (Solexa), or polony amplification (Agencourt/Applied Biosystems).

For sequencing by ligation, labeled nucleic acid fragments are hybridized and identified to determine the sequence of a target nucleic acid molecule. For sequencing by synthesis (SBS), labeled nucleotides are used to determine the sequence of a target nucleic acid molecule. An SBS approach is shown schematically in FIG. 2A. A target nucleic acid molecule is hybridized with a primer and incubated in the presence of a polymerase and a labeled nucleotide containing a blocking group. The primer is extended such that the nucleotide is incorporated. The presence of the blocking group permits only one-round of incorporation, that is, the incorporation of a single nucleotide. The presence of the label permits identification of the incorporated nucleotide. Either single bases can be added or, alternatively, all four bases can be added simultaneously, particularly when each base is associated with a distinguishable label. After identifying, the incorporated nucleotide by its corresponding label, both the label and the blocking group can be removed, thereby allowing a subsequent round of incorporation and identification. Thus, it is desirable to have conveniently cleavable linkers linking the label to the base, such as those disclosed herein, in particular peptide linkers. Additionally, it is advantageous to use a removable blocking group so that multiple rounds of identification can be performed, thereby permitting identification of at least a portion of the target nucleic acid sequence. The compositions and methods disclosed herein are particularly useful for such an SBS approach. In addition, the compositions and methods can be particularly useful for sequencing from an array, where multiple sequences can be "read" simultaneously from multiple positions on the array since each nucleotide at each position can be identified based on its identifiable label.

The oligonucleotides, nucleosides and nucleotides described herein can be particularly useful for nucleotide sequence characterization or sequence analysis. Reversible labeling, reversible termination or a combination thereof can allow accurate sequencing analysis to be efficiently performed. Methods for manual or automated sequencing are well known in the art and include, but are not limited to, Sanger sequencing, pyrosequencing, sequencing by hybridization, sequencing by ligation and the like. Sequencing methods can be preformed manually or using automated methods. Furthermore, the oligonucleotides, nucleosides and nucleotides set forth herein can be used to prepare nucleic acids for sequencing using commercially available methods such as automated Sanger sequencing (available from Applied Biosystems, Foster City Calif.) or pyrosequencing (available from 454 Lifesciences, Branford, Conn. and Roche Diagnostics, Basel, Switzerland); for sequencing by synthesis methods currently being developed by Solexa (Hayward, Calif.) or Helicos (Cambridge, Mass.) or sequencing by ligation methods being developed by Applied Biosystems in its Agencourt platform (see also Ronaghi et al., *Science* 281:363 (1998); Dressman et al., *Proc. Natl. Sci. USA* 100:8817-8822 (2003); Mitra et al., *Proc. Natl. Sci. USA* 100:55926-5931 (2003)).

A nucleic acid sample obtained using methods described herein can be amplified prior to analysis. A particularly useful method is emulsion PCR. However, amplification need not be carried out if the sample provides sufficient quantity to suit the particular method being used. A nucleic acid sample to be sequenced can be attached to a solid phase using methods and substrates described elsewhere herein or otherwise known in the art. The sample will typically be attached as a population of separate nucleic acids, such as those encoding genome fragments, that can be distinguished from each other. Microarrays are particularly useful for sequence analysis.

A population of nucleic acids can be sequenced using methods in which a primer is hybridized to each nucleic acid such that the nucleic acids form templates and modification of the primer occurs in a template directed fashion. The modification can be detected to determine the sequence of the template. For example, the primers can be modified by extension using a polymerase and extension of the primers can be monitored under conditions that allow the identity and location of particular nucleotides to be determined. For example, extension can be monitored and sequence of the template nucleic acids determined using pyrosequencing which is described in further detail below, in US 2005/0130173; US 2006/0134633; U.S. Pat. No. 4,971,903; U.S. Pat. No. 6,258,568 and U.S. Pat. No. 6,210,891, each of which is incorporated herein by reference and is also commercially available, see above. Extension can also be monitored according to addition of labeled nucleotide analogs by a polymerase, using methods described, for example, elsewhere herein and in U.S. Pat. No. 4,863,849; U.S. Pat. No. 5,302,509; U.S. Pat. No. 5,763,594; U.S. Pat. No. 5,798,210; U.S. Pat. No. 6,001,566; U.S. Pat. No. 6,664,079; US 2005/0037398; and U.S. Pat. No. 7,057,026, each of which is incorporated herein by reference. Polymerases useful in sequencing methods are typically polymerase enzymes derived from natural sources. It will be understood that polymerases can be modified to alter their specificity for modified nucleotides as described, for example, in WO/01/23411; U.S. Pat. No. 5,939,292; and WO 05/024010, each of which is incorporated herein by reference. Furthermore, polymerases need not be derived from biological systems.

A further modification of primers that can be used to determine the sequence of templates to which they are hybridized is ligation. Such methods are referred to as sequencing by ligation and are described, for example, in Shendure et al. *Science* 309:1728-1732 (2005); U.S. Pat. No. 5,599,675; and U.S. Pat. No. 5,750,341, each of which is incorporated herein by reference. It will be understood that primers need not be modified in order to determine the sequence of the template to which they are attached. For example, sequences of template nucleic acids can be determined using methods of sequencing by hybridization such as those described in U.S. Pat. No. 6,090,549; U.S. Pat. No. 6,401,267 and U.S. Pat. No. 6,620,584. It is understood that many of the uses of compositions of the present invention can be applied to both sequencing by synthesis (SBS) or single base extension (SBE), discussed in more detail below), since both utilize extension reactions that can incorporate a composition of the invention, including nucleotides with cleavable peptide linkers and/or blocking groups, either removable or not.

In a particular embodiment, arrayed nucleic acid probes can be modified while hybridized to target nucleic acids for detection. A nucleic acid, nucleotide or nucleoside having a reversible blocking group on a 2', 3' or 4' hydroxyl, a peptide linked label or a combination thereof can be used in such methods. For example the nucleic acid, nucleotide or nucleoside can be included in a probe or nucleic acid. Additionally or alternatively the nucleic acid, nucleotide or nucleoside can be used to modify the probe. Such embodiments, include, for example, those utilizing allele-specific primer extension (ASPE), SBE, oligonucleotide ligation amplification (OLA), extension ligation, invader technology, probe cleavage or pyrosequencing as described in U.S. Pat. No. 6,355,431 B1, U.S. Ser. No. 10/177,727 and/or below. Thus, the invention can be carried out in a mode wherein an immobilized probe is modified instead of a nucleic acid captured by a probe. Alternatively, detection can include modification of the nucleic acids while hybridized to probes. Exemplary modifications include those that are catalyzed by an enzyme such as a polymerase. A useful modification can be incorporation of one or more nucleotides or nucleotide analogs to a primer hybridized to a template strand, wherein the primer can be either the probe or nucleic acid in a probe-nucleic acid-fragment hybrid.

Extension assays are useful for detection of alleles, mutations or other nucleic acid features. Extension assays are generally carried out by modifying the 3' end of a first nucleic acid when hybridized to a second nucleic acid. The second nucleic acid can act as a template directing the type of modification, for example, by base pairing interactions that occur during polymerase-based extension of the first nucleic acid to incorporate one or more nucleotide. Polymerase extension assays are particularly useful, for example, due to the relative high-fidelity of polymerases and their relative ease of implementation. Extension assays can be carried out to modify nucleic acid probes that have free 3' ends, for example, when bound to a substrate such as an array. Exemplary approaches that can be used include, for example, allele-specific primer extension (ASPE), single base extension (SBE), or pyrosequencing. A nucleic acid, nucleotide or nucleoside having a reversible blocking group on a 2', 3' or 4' hydroxyl, a peptide linked label or a combination thereof can be used in such methods. For example the nucleic acid, nucleotide or nucleoside can be included in the first nucleic acid or the second nucleic acid. Additionally or alternatively, the nucleic acid, nucleotide or nucleoside can be used to modify the free 3' ends in the extension reactions.

In particular embodiments, single base extension (SBE) can be used for detection of a typable locus such as an allele, mutations or other nucleic acid features. The compositions of the present invention are useful in an SBE method, in particular, a nucleoside or nucleotide containing a peptide linker, allowing cleavage and removal of a label, and/or terminator blocking group, either removable or non-removable. Briefly, SBE utilizes an extension probe that hybridizes to a target genome fragment at a location that is proximal or adjacent to a detection position, the detection position being indicative of a particular typable locus. A polymerase is used to extend the 3' end of the probe with a nucleotide analog labeled with a detection label such as those described previously herein. Based on the fidelity of the enzyme, a nucleotide is only incorporated into the extension probe if it is complementary to the detection position in the target nucleic acid. If desired, the nucleotide can be derivatized such that no further extensions can occur, as disclosed herein using a blocking group, including reversible blocking groups, and thus only a single nucleotide is added. The presence of the labeled nucleotide in the extended probe can be detected for example, at a particular location in an array and the added nucleotide identified to determine the identity of the typable locus. SBE can be carried out under known conditions such as those described in U.S. patent application Ser. No. 09/425,633. A labeled nucleotide can be detected using methods such as those set forth above or described elsewhere such as Syvanen et al., *Genomics* 8:684-692 (1990); Syvanen et al., *Human Mutation* 3:172-179 (1994); U.S. Pat. Nos. 5,846,710 and 5,888,819; Pastinen et al., *Genomics Res.* 7(6):606-614 (1997).

A nucleotide analog useful for SBS or SBE detection can include a dideoxynucleoside-triphosphate (also called deoxynucleotides or ddNTPs, i.e. ddATP, ddTTP, ddCTP and ddGTP), or other nucleotide analogs that are derivatized to be chain terminating, as disclosed herein. For example, the nucleotides containing cleavable peptide linkers linking a dye and/or blocking groups, either removable or not, can be used for SBS or SBE. The use of labeled chain terminating nucleotides is useful, for example, in reactions having more than one type of dNTP present so as to prevent false positives due to extension beyond the detection position. Exemplary analogs are dideoxy-triphosphate nucleotides (ddNTPs) or acyclo terminators (Perkin Elmer, Foster City, Calif.). Generally, a set of nucleotides comprising ddATP, ddCTP, ddGTP and ddTTP can be used, at least one of which includes a label. If desired for a particular application, a set of nucleotides in which all four are labeled can be used. The labels can all be the same or, alternatively, different nucleotide types can have different labels. As will be appreciated by those in the art, any number of nucleotides or analogs thereof can be added to a primer, as long as a polymerase enzyme incorporates a particular nucleotide of interest at an interrogation position that is indicative of a typable locus.

A nucleotide used in an SBS method or an SBE detection method can further include, for example, a detectable label, which can be either a primary or secondary detectable label. Any of a variety of the nucleic acid labels set forth herein can be used in an SBS method or an SBE detection method. The use of secondary labels can also facilitate the removal of unextended probes in particular embodiments. The labels can be attached via a peptide linkage, if desired.

The solution for SBE, similar to an SBS method, can also include an extension enzyme, such as a DMA polymerase. Suitable DNA polymerases include, but are not limited to, the Klenow fragment of DNA polymerase I, SEQUENASE™ 1.0 and SEQUENASE™ 2.0 (U.S. Biochemical), T5 DNA polymerase, Phi29 DNA polymerase, Thermosequenase™ (Taq with the Tabor-Richardson mutation) and others known in the art or described herein. Modified versions of these polymerases that have improved ability to incorporate a nucleotide analog of the invention can also be used. If the nucleotide is complementary to the base of the detection position of the target sequence, which is adjacent to the extension primer, the extension enzyme will add it to the extension primer. Thus, the extension primer is modified, i.e. extended, to form a modified primer.

As will be appreciated by those in the art, the configuration of an SBS method or SBE reaction can take on any of several forms. In particular embodiments, the reaction can be done in solution, and then the newly synthesized strands, with the base-specific detectable labels, can be detected. For example, they can be directly hybridized to capture probes that are complementary to the extension primers, and the presence of the label can then be detected. Such a configuration is useful, for example, when genome fragments are arrayed as capture probes. Alternatively, the SBS or SBE reaction can occur on a surface. For example, a genome fragment can be captured using a first capture probe that hybridizes to a first target domain of the fragment, and the reaction can proceed such that the probe is modified.

The determination of the base at the detection position can proceed in any of several ways. In a particular embodiment, a mixed reaction can be run with two, three or four different nucleotides, each with a different label. In this embodiment, the label on the probe can be distinguished from non incorporated labels to determine which nucleotide has been incorporated into the probe. Alternatively, discrete reactions can be run each with a different labeled nucleotide. The same label can be used for all of the different nucleotides or different labels can be used for each type. The reaction can be carried out either by using a single substrate bound probe and sequential reactions, or by exposing the same reaction to multiple substrate-bound probes. For example dATP can be added to a probe-target hybrid, and the generation of a signal evaluated; the dATP can be removed and dTTP added, etc. Alternatively, four arrays can be used; the first is reacted with dATP, the second with dTTP, etc., and the presence or absence of a signal evaluated in each array.

Single base sequencing is an extension assay that can be carried out as set forth above for SBE with the exception that one or more non-chain terminating nucleotides are included in the extension reaction. Thus, in accordance with the invention, one or more non-chain terminating nucleotides can be included in an SBE reaction including, for example, those set forth above.

An exemplary embodiment of single base sequencing is to carry out two separate reactions on two separate probe populations. The two separate reactions are advantageously carried out using a single label; however, if desired more than one type of label can be used. The first reaction can include 2 different labeled nucleotides that are extendable and capable of hybridizing to 2 of the 4 naturally occurring nucleotides in the genomic DNA. The second reaction can include 2 different nucleotides, the nucleotides being labeled and capable of hybridizing to the other 2 naturally occurring nucleotides in the target nucleic acid. Each of the two reactions can be devoid of the nucleotides found in the other reaction or can include chain terminating analogs of the nucleotides found in the other reaction. By way of example, the first reaction (hot AC reaction) can include dATP-biotin and dCTP-biotin. This first reaction can lack GTP, UTP and TIP. Alternatively, the first reaction can include dideoxyGTP and dideoxyUTP (or dideoxyGTP and dideoxyTTP). Continuing with the example, the second reaction (hot GU reaction) can include dGTP-biotin and dUTP-biotin (or dGTP-biotin and dTTP-biotin). This second reaction can lack CTP or ATP. Alternatively, the second reaction can include dideoxyCTP and dideoxyATP. This exemplary labeling scheme allows detection of almost 80% of naturally occurring human SNPs since the most abundant human SNPs are A/G and C/T polymorphisms.

ASPE is an extension assay that utilizes extension probes that differ in nucleotide composition at their 3' end. An ASPE method can be performed using a nucleoside or nucleotide containing a cleavable linker such as a protease cleavable linker so that a label can be removed after a probe is detected. This allows further use of the probes or verification that the signal detected was due to the label that has now been removed. Briefly, ASPE can be carried out by hybridizing a target nucleic acid to an extension probe having a 3' sequence portion that is complementary to a detection position and a 5' portion that is complementary to a sequence that is adjacent to the detection position. Template directed modification of the 3' portion of the probe, for example, by addition of a labeled nucleotide by a polymerase yields a labeled extension product, but only if the template includes the target sequence. The presence of such a labeled primer-extension product can then be detected, for example, based on its location in an array to indicate the presence of a particular typable locus.

In particular embodiments, ASPE can be carried out with multiple extension probes that have similar 5' ends such that they anneal adjacent to the same detection position in a target nucleic acid but different 3' ends, such that only probes having a 3' end that complements the detection position are modified by a polymerase. A probe having a 3' terminal base that is complementary to a particular detection position is referred to as a perfect match (PM) probe for the position, whereas probes that have a 3' terminal mismatch base and are not capable of being extended in an ASPE reaction are mismatch (MM) probes for the position. The presence of the labeled nucleotide in the PM probe can be detected and the 3' sequence of the probe determined to identify a particular typable locus. An ASPE reaction can include 1, 2, or 3 different MM probes, for example, at discrete array locations, the number being chosen depending upon the diversity occurring at the particular locus being assayed. For example, two probes can be used to determine which of 2 alleles for a particular locus are present in a sample, whereas three different probes can be used to distinguish the alleles of a 3-allele locus.

In particular embodiments, an ASPE reaction can include a nucleotide analog that is derivatized to be chain terminating. Thus, a PM probe in a probe-fragment hybrid can be modified to incorporate a single nucleotide analog without further extension. Exemplary chain terminating nucleotide analogs include, without limitation, those set forth above in regard to the SBE reaction. Reversible or non-reversible chain terminating analogs can be used. Furthermore, one or more nucleotides used in an ASPE reaction whether or not they are chain terminating can include a detection label such as those described previously herein. The label can be removable by being attached via a peptide linker, if desired. For example, an ASPE reaction can include a single biotin labeled dNTP. If desired, more than one nucleotide in an ASPE reaction can be labeled. For example, reaction conditions can be modified to include biotinylated dCTP as well as biotinylated dGTP and biotinylated dTTP. An ASPE reaction can be carried out in the presence of all four nucleotides A, C, T, and G or in the presence of a subset of these nucleotides including, for example, a subset that lacks substantial amounts of one or more of A, C, T or G.

Pyrosequencing is an extension assay that can be used to add one or more nucleotides to a detection position(s); it is similar to SBE except that identification of typable loci is based on detection of a reaction product, pyrophosphate (PPi), produced during the addition of a dNTP to an extended probe, rather than on a label attached to the nucleotide. One molecule of PPi is produced per dNTP added to the extension primer. That is, by running sequential reactions with each of the nucleotides, and monitoring the reaction products, the identity of the added base is determined. Pyrosequencing can be used in the invention using conditions such as those described in US 2002/0001801. A nucleotide used in a pyrosequencing reaction can include a 2', 3' or 4' reversible blocking group. An advantage of using reversible blocking groups in pyrosequencing is that each nucleotide in a homopolymeric sequence region can be discretely detected in separate reaction steps. Absent reversible terminating groups, a primer will be extended all the way through a homopolymeric region in a single reaction step if the appropriate nucleotide is present. In this situation, determination of the number of nucleotides added requires quantification of individual pyrophosphate units, which is not always convenient or practical.

Detection with oligonucleotide ligation amplification (OLA) involves the template-dependent ligation of two smaller probes into a single long probe, using a genome-fragment target sequence as the template. In a particular embodiment, a single-stranded target sequence includes a first target domain and a second target domain, which are adjacent and contiguous. A first OLA probe and a second OLA probe can be hybridized to complementary sequences of the respective target domains. The two OLA probes are then covalently attached to each other to form a modified probe. In embodiments where the probes hybridize directly adjacent to each other, covalent linkage can occur via a ligase. In one embodiment one of the ligation probes may be attached to a surface such as an array or a particle. In another embodiment both ligation probes may be attached to a surface such as an array or a particle. One or both probes can include a nucleoside having a peptide linked label. Accordingly, the presence of the ligated product can be determined by detecting the label. Furthermore, the 3' nucleoside of one or both probes can include a 2', 3' or 4' reversible blocking group. Thus ligation can be inhibited until the blocking group is removed, thereby providing a further level of control over a detection reaction with the added benefit of improved specificity.

Alternatively, an extension-ligation assay can be used wherein hybridized probes are non-contiguous and one or more nucleotides are added along with one or more agents that join the probes via the added nucleotides. Exemplary agents include, for example, polymerases and ligases. If desired, hybrids between modified probes and targets can be denatured, and the process repeated for amplification leading to generation of a pool of ligated probes. As above, these extension-ligation probes can be but need not be attached to a surface such as an array or a particle. Further conditions for extension ligation assay that are useful in the invention are described, for example, in U.S. Pat. No. 6,355,431 B1 and U.S. application Ser. No. 10/177,727. One or both of the probes can include nucleosides having 2', 3' or 4' reversible blocking group, a peptide linked label or combination thereof as exemplified above for OLA reactions. Furthermore, one or more nucleotide added by extension in an extension-ligation assay can include a 2', 3' or 4' reversible blocking group, a peptide linked label or combination thereof.

A modified version of OLA is referred to as the ligation chain reaction (LCR) when double-stranded genome fragment targets are used. In LCR, the target sequence can be denatured, and two sets of probes added: one set as outlined above for one strand of the target, and a separate set (i.e. third and fourth primer probe nucleic acids) for the other strand of the target. Conditions can be used in which the first and second probes hybridize to the target and are modified to form an extended probe. Following denaturation of the target-modified probe hybrid, the modified probe can be used as a template. In addition to the second target sequence, for the attachment of the third and fourth probes. Similarly, the ligated third and fourth probes can serve as a template for the attachment of the first and second probes, in addition to the first target strand. In this way, an exponential, rather than just a linear, amplification can occur when the process of denaturation and ligation is repeated. One or both LCR probes can include nucleosides having 2', 3' or 4' reversible blocking group, a peptide linked label or combination thereof as exemplified above for OLA reactions.

Typable loci can be detected in a method of the invention using rolling circle amplification (RCA). In a first embodiment, a single probe can be hybridized to a genome fragment target such that the probe is circularized while hybridized to the target. Each terminus of the probe hybridizes adjacently on the target nucleic acid and addition of a polymerase results in extension of the circular probe. However, since the probe has no terminus, the polymerase continues to extend the probe repeatedly. This results in amplification of the circular probe. Following RCA the amplified circular probe can be detected. This can be accomplished in a variety of ways; for example, the primer can be labeled or the polymerase can incorporate labeled nucleotides and labeled product detected by a capture probe in a detection array. Rolling-circle amplification can be carried out under conditions such as those generally described in U.S. Pat. No. 6,355,431, Baner et al. (1998) *Nuc. Acids Res.* 26:5073-5078; Barany, F. (1991) *Proc. Natl. Acad. Sci. USA* 88:189-193; and Lizardi et al. (1998) *Nat Genet.* 19:225-232. An RCA probe can include nucleosides having 2', 3' or 4' reversible blocking group, a peptide linked label or combination thereof as exemplified above for OLA reactions.

A padlock probe used in the invention can further include other characteristics such as an adaptor sequence, restriction site for cleaving concatamers, a label sequence or a priming site for priming the RCA reaction as described, for example, in U.S. Pat. No. 6,355,431 B1. This same patent also describes padlock probe methods that can be used to detect typable loci of genome fragment targets in a method of the invention.

In particular embodiments a nucleic acid, nucleoside or nucleotide useful in the invention can include a label. As set forth herein, the label can be attached via a peptide linker. As used herein, a "label" refers to one or more atoms that can be specifically detected to indicate the presence of a substance to which the one or more atoms is attached. A label can be a primary label that is directly detectable or secondary label that can be indirectly detected, for example, via direct or indirect interaction with a primary label. Exemplary primary labels include, without limitation, an isotopic label such as a naturally non-abundant radioactive or heavy isotope, including but not limited to $^{14}C$, $^{123}I$, $^{124}I$, $^{125}I$, $^{131}I$, $^{32}P$, $^{35}S$, and $^{3}H$; chromophore; luminophore; fluorophore; calorimetric agent; magnetic substance; electron-rich material such as a metal; electrochemiluminescent label such as Ru(bpy)32+; or moiety that can be detected based on a nuclear magnetic, paramagnetic, electrical, charge to mass, or thermal characteristic. Fluorophores that are useful in the invention include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, *Molecular Probes Handbook*, (Eugene, Oreg.) 6th Edition; The Synthegen catalog (Houston, Tex.), Lakowicz, *Principles of Fluorescence Spectroscopy*, 2nd Ed., Plenum Press New York (1999), or WO 98/59066. Labels can also include enzymes such as horseradish peroxidase or alkaline phosphatase or particles such as magnetic particles or optically encoded nanoparticles.

Exemplary secondary labels are binding moieties. A binding moiety can be attached to a nucleic acid to allow detection or isolation of the nucleic acid via specific affinity for a receptor. Specific affinity between two binding partners is understood to mean preferential binding of one partner to another compared to binding of the partner to other components or contaminants in the system. Binding partners that are specifically bound typically remain bound under the detection or separation conditions described herein, including wash steps to remove non-specific binding. Depending upon the particular binding conditions used, the dissociation constants of the pair can be, for example, less than about $10^{-4}$, $10^{-5}$, $10^{-6}$, $10^{-7}$, $10^{-8}$, $10^{-9}$, $10^{-10}$, $10^{-11}$, or $10^{-12}$ $M^{-1}$.

Exemplary pairs of binding moieties and receptors that can be used as labels in the invention include, without limitation, antigen and immunoglobulin or active fragments thereof such as FAbs; immunoglobulin and immunoglobulin (or active fragments, respectively); avidin and biotin, or analogs thereof having specificity for avidin such as imino-biotin; streptavidin and biotin, or analogs thereof having specificity for streptavidin such as imino-biotin; carbohydrates and lectins; and other known proteins and their ligands. It will be understood that either partner in the above-described pairs can be attached to a nucleic acid and detected or isolated based on binding to the respective partner. It will be further understood that several moieties that can be attached to a nucleic acid can function as both primary and secondary labels, in a method of the invention. For example, strepatvidin-phycoerythrin can be detected as a primary label due to fluorescence from the phycoerythrin moiety or it can be detected as a secondary label due to its affinity for anti-streptavidin antibodies, as set forth in further detail below in regard to signal amplification methods.

In a particular embodiment, the secondary label can be a chemically modifiable moiety. In this embodiment, labels having reactive functional groups can be incorporated into a nucleic acid, nucleoside or nucleotide. The functional group can be subsequently covalently reacted with a primary label. Suitable functional groups include, but are not limited to, amino groups, carboxy groups, maleimide groups, oxo groups and thiol groups.

Signal amplification can be earned out using a nucleic acid labeled by streptavidin-phycoerythrin (SAPE) and a biotinylated anti-SAPE antibody. In one embodiment, a three step protocol can be employed in which arrayed probes that have been modified to incorporate biotin are first incubated with streptavidin-phycoerythrin (SAPE), followed by incubation with a biotinylated anti-streptavidin antibody, and finally incubation with SAPE again. This process creates a cascading amplification sandwich since streptavidin has multiple antibody binding sites and the antibody has multiple biotins. Those skilled in the art will recognize from the teaching herein that other receptors such as avidin, modified versions of avidin, or antibodies can be used in an amplification complex and that different labels can be used such as Cy3, Cy5 or others set forth previously herein. Further exemplary signal amplification techniques and components that can be used in the invention are described, for example, in U.S. Pat. No. 6,203,989 B1.

As disclosed herein, a variety of fluorescent dyes are particularly useful labels in compositions and methods of the invention, including, but not limited to, FAM, Bodipy, TAMRA, Alexa, and the like (see Example IV). These and other suitable fluorescent moieties are well known to those skilled in the art (see Hermanson, Bioconjugate Techniques, pp. 297-364, Academic Press, San Diego (1996); Molecular Probes, Eugene Oreg.). Rhodamine derivatives include, for example, tetramethylrhodamine, rhodamine B, rhodamine 6G, sulforhodamine B, Texas Red (sulforhodamine 101), rhodamine 110, and derivatives thereof such as tetramethylrhodamine-5- (or 6), lissamine rhodamine B, and the like. Other suitable fluorophores include 7-nitrobenz-2-oxa-1,3-diazole (NBD.

Additional exemplary fluorophores include, for example, fluorescein, and derivatives thereof. Other flurophores include napthalenes such as dansyl (5-dimethylaminonapthalene-1-sulfonyl). Additional fluorophores include coumarin derivatives such as 7-amino-4-methylcoumarin-3-acetic acid (AMCA), 7-diethylamino-3-[(4'-(iodoacetyl)amino)-phenyl]-4-methylcoumarin (DCIA), Alexa fluor dyes (Molecular Probes), and the like.

Other fluorophores include 4,4-difluoro-4-bora-3a,4a-diaza-s-indacene (BODIPY™) and derivatives thereof (Molecular Probes; Eugene Oreg.). Further fluorophores include pyrenes and sulfonated pyrenes such as Cascade Blue™ and derivatives thereof, including 8-methoxypyrene-1,3,6-trisulfonic acid, and the like. Additional fluorophores include pyridyloxazole derivatives and dapoxyl derivatives (Molecular Probes). Additional fluorophores include Lucifer Yellow (3,6-disulfonate-4-amino-naphthalimide) and derivatives thereof. CyDye™ fluorescent dyes (Amersham Pharmacia Biotech; Piscataway N.J.) can also be used. Energy transfer dyes can additionally be used such as those described in U.S. Pat. No. 7,015,000 or U.S. Pat. No. 6,573,047, each of which is incorporated herein by reference.

In certain aspects of the invention, a protease cleavable linker is used to link a dye to an RT-NTP so that the dye can be cleaved and removed. A protease can be used to cleave a cleavable linker having a suitable recognition sequence for the protease. Particularly useful proteases are endopeptidases such as chymotrypsin, proteinase K, subtilisin, trypsin, factor Xa, tobacco etch virus (TEV) protease, *Staphylococcus aureus* protease, submaxillaris protease, Kallikrein protease, matrix metalloprotease-2 (MMP-2) and the like. The protease can be selected based on the incorporation of a particular cleavable recognition sequence into the linker.

As used herein, the term "protease" is intended to mean an agent that catalyzes the cleavage of peptide bonds in a protein or peptide. Some proteases are non-sequence specific proteases. Generally, for the methods disclosed herein, the protease has sequence specificity, splitting a peptide bond of a protein based on the presence of a particular amino acid sequence in the protein. A protease can be characterized according to the location in a protein where it cleaves, an endoprotease cleaving a protein between internal amino acids of an amino acid chain and an exoprotease cleaving a protein to remove an amino acid from the end of an amino acid chain. In the peptide linkers of the compositions herein, an endoprotease is used. A protease can be characterized according to mechanism of action, being identified, for example, as a serine protease, cysteine (thiol) protease, aspartic (acid) protease, metalloprotease or mixed protease depending on the principal amino acid participating in catalysts. A protease can also be classified based on the action pattern, examples of which include an aminopeptidase which cleaves an amino acid from the amino end of a protein, carboxypeptidase which cleaves an amino acid from the carboxyl end of a protein, dipeptidyl peptidase which cleaves two amino acids from an end of a protein, dipeptidase which splits a dipeptide and tripeptidase which cleaves an amino acid from a tripeptide. Typically, a protease is a protein enzyme. However, non-protein agents capable of catalyzing the cleavage of peptide bonds in a protein, especially in a sequence specific manner are also useful in the invention.

As used herein, the term "activity," when used in reference to a protease, is intended to mean binding of the protease to a protease substrate or hydrolysis of the protease substrate or both. The activity can be indicated, for example, as binding specificity, catalytic activity or a combination thereof. The activity of a protease can be identified qualitatively or quantitatively in accordance with the compositions and methods disclosed herein. Exemplary qualitative measures of protease activity include, without limitation, identification of a substrate cleaved in the presence of the protease, identification of a change in substrate cleavage due to presence of another agent such as an inhibitor or activator, identification of an amino acid sequence that is recognized by the protease, identification of the composition of a substrate recognized by the protease or identification of the composition of a proteolytic product produced by the protease. Activity can be quantitatively expressed as units per milligram, of enzyme (specific activity) or as molecules of substrate transformed per minute per molecule of enzyme (molecular activity). The conventional unit of enzyme activity is the International Unit (IU), equal to one micromole of substrate transformed per minute, A proposed coherent Système Internationale (SI) unit is the katal (kat), equal to one mole of substrate transformed per second.

As used herein the term, "protease substrate" is intended to mean a molecule that can be cleaved by a protease. A protease substrate is typically a protein, protein moiety or peptide having an amino acid sequence that is recognized by a protease. A protease can recognize the amino acid sequence of a protease substrate due to the specific sequence of side chains or due to properties generic to proteins. A protease substrate can also be a protein mimetic or non-protein molecule that is capable of being cleaved or otherwise covalently modified by a protease.

Exemplary proteases, corresponding peptide substrates and commercial source are shown in Table 2.

TABLE 2

Proteases and their cleavage preferences.

| Protease | Peptide (cleavage site indicated with dash) | Company |
|---|---|---|
| Thrombin | LVPR-GS | Amersham, Novagen, Sigma, Roche |
| Factor Xa | IEGR-X | Amersham, NEB, Roche |
| Enterokinase | DDDDK-X | NEB, Novagen, Roche |
| TEV protease | ENLYFQ-G | Invitrogen |
| PreScission | LEVLFQ-GP | Amersham |
| HRV 3C Protease | LEVLFQ-GP | Novagen |
| Trypsin | R-X, K-X | |
| Endoproteinase Asp-N | X-D | |
| Chymotrypsin | Y-X, F-X, W-X | |
| Endoproteinase Glu-C | E-X | |
| Endoproteinase Arg-C | R-X | |
| Endoproteinase Lys-C | K-X | |

Enzymatically cleavable linkers used in the invention are generally peptides. Peptide synthesis can be carried out using standard solid phase or solution phase chemistry, as desired. Methods for peptide synthesis are well known to those skilled in the art (Fodor et. al., Science 251:767 (1991); Gallop et al., J. Med. Chem. 37:1233-1251 (1994); Gordon et al., J. Med. Chem. 37:1385-1401 (1994). It is understood that a peptide linker can be synthesized and then added to the NTP as a peptide or can be synthesized by sequentially adding amino acids and then a dye.

The peptide sequences for a specific protease can be selected, for example, by synthesizing appropriate substrate peptides and optimizing those peptides, as disclosed herein (see Example III). The peptide sequences for specific peptides can be selected, for example, by screening peptide libraries. The libraries can contain random peptide sequences generated using combinatorial chemistry, as described herein or well known in the art, or other well known methods such as phage display of random peptide libraries (see U.S. Pat. No. 6,068,829; Smith and Scott, Meth. Enzymol. 217:228-257 (1993); Scott and Smith, Science 249:386-390 (1990); Koivunen et al., Biotechnology 13:265-270 (1995) Koivunen et al. Meth. Enzymol. 245:346-369 (1994), each of which is incorporated herein by reference).

In addition, focused peptide libraries can be used to optimize a peptide sequence for protease cleavage based on existing known peptide sequences. The protease recognizes the peptide portion of the molecule and hydrolyzes the peptide at a specific cleavage site in the amino acid sequence, resulting in removal of dye molecules attached via a peptide linker, as disclosed herein. If desired, a spacer can be used between the nucleoside or nucleotide base and the linker, or between the linker and the label. Different lengths of spacers can be used in order to increase the peptide availability towards the protease and increase the efficiency and fidelity of polymerases. Exemplary spacers include, for example, polyethyleneglycol or other suitable spacers.

Figure 15:
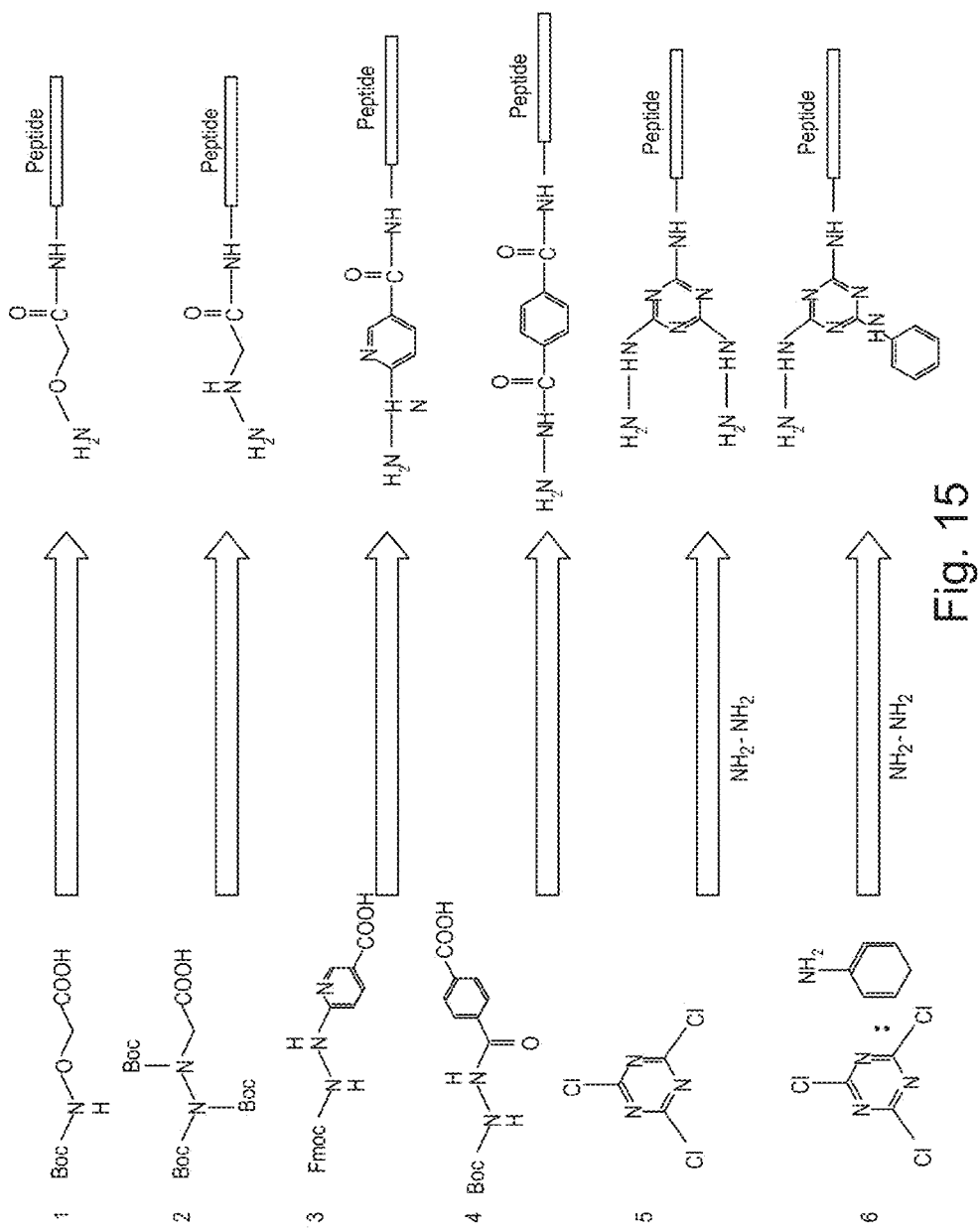
FIG. 15 shows different aldehyde reactive groups for peptide modification.
Figure 16:
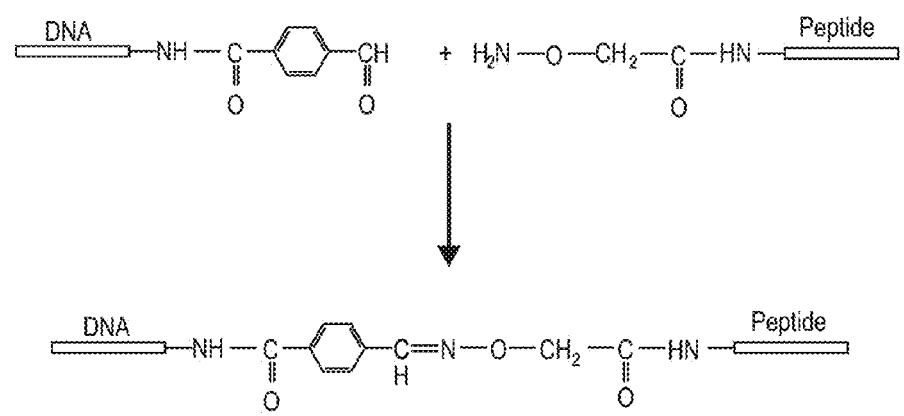
FIG. 16 shows exemplary coupling chemistry for a peptide linker.

Table 3 shows exemplary coupling chemistries, with the corresponding modification and reactive groups on the respective peptide and nucleotide. Exemplary chemistry for coupling a peptide to a nucleotide or nucleic acid is described, for example, in U.S. publication 2005/0136406, which is incorporated herein by reference. Exemplary chemistries for coupling a peptide are shown in FIGS. 15 and 16). At the end of the synthesis, Boc-protected aminooxyacetic acid is attached using standard peptide coupling conditions or other aldehyde reactive groups as shown in FIG. 15. In order to find the best aldehyde reactive group for peptide modification, six different aldehyde reactive groups are attached to the N-terminus of a peptide (FIG. 15). The conjugation reaction is efficient for all peptide modifying groups tested (over 90% yield of conjugate).

Additional chemistries that are mild reactions that are performed in aqueous solution include azide plus alkyne and azide plus phosphine (see, for example, Kolb et al., Angew. Chem. 40:2004-2021 (2001); Goodall and Hayes, Chem. Soc. Rev. 35:280-312 (2006); Saxon et al., Org. Lett. 2:2141-2143 (2000); Nilsson et al., Org. Lett. 2:1939-1941 (2000); Nilsson et al., B. L.; Kiesling, L. L.; Raines, R. T, Org. Lett. 3:9-12 (2001); Nilsson et al., J. Am. Chem. Soc. 125:5268-5269 (2003), each of which is incorporated herein by reference.

TABLE 3

Exemplary coupling chemistries for linking a peptide to a nucleotide.

| Modified peptide | Modified nucleotide |
|---|---|
| 1. Cl-triazine-Cl (cyanuric chloride, with three Cl substituents on triazine ring) | NH2 |
| S=C=N—C6H4—N=C=S | NH2 |
| CO2H(CH2)2CO2H | NH2 |
| 4-nitrophenyl chloroformate (O=C(OCCl)—C6H4—NO2) | NH2 |
| SuO-C(=O)-pyridine-NH—N=C(CH3)2 | CHO |
| 4-nitrophenyl chloroformate (O=C(OCCl)—C6H4—NO2) | NH2 |
| NHS | NH2 |
| NH2 | CHO |

The peptide sequence can also be optimized to achieve the best activity for both protease cleavage and/or incorporation by polymerase enzymes or other catalysts, as disclosed herein. Exemplary optimization of protease cleavage activity is described in Example III. Similarly, optimization of a peptide substrate, using naturally or non-naturally occurring amino acids, can be performed for my desired protease.

As set forth above, a peptide linker can be cleaved using an exoprotease or endoprotease to remove a label form a nucleotide or oligonucleotide. In particular embodiments, a label can be removed using a combination of an endoprotease and exoprotease. For example, a peptide linker on a nucleotide or oligonucleotide can be cleaved internally using an endoprotease and any remaining residues on the nucleotide or oligonucleotide can be removed with an exoprotease. Such methods can be advantageous in order to remove any linker fragments that are undesirable, for example, due to reducing subsequent incorporation of nucleotides in a sequencing reaction. Such methods can also be advantageous when the presence of a label on a peptide prevents exoprotease activity. In such cases the label can be removed due to the activity of endoprotease activity and the remaining linker residues removed by the exoprotease.

Methods useful for modifying a nucleoside or nucleotide to contain an enzymatically cleavable linker such as a peptide linker and/or a blocking group utilize chemistries well known to those skilled in the art. Such methods are described herein, and exemplary synthesis methods are described in Example I.

The invention additionally provides a kit containing one or more RT-NTPs. The kit can contain, for example, a set of four RT-NTPs for each ribonucleoside, where each of the NTPs has a different dye so that each of the ribonucleosides can be distinguished (see Example IV). In another embodiment, a kit can include a suitable protease if the RT-NTP contains an enzymatically cleavable linker. In addition, a kit can include other reagents, such as a phosphatase for removing a phosphate blocking group. The contents of the kit of the invention, for example are contained in packaging material, and, if desired, a sterile, contaminant-free environment. In addition, the packaging material contains instructions indicating how the materials within the kit can be employed. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

A kit of the invention can include a nucleoside or nucleotide molecule containing a label linked to the molecule by an enzymatically cleavable peptide linker. The label can be linked to the base of the molecule. The nucleoside or nucleotide can further comprise a blocking group. The blocking group can be removable. The blocking group can be attached at the 2', 3' or 4'-position of the sugar moiety of the molecule. A removable blocking group can be selected, for example, from those shown in FIG. 1A. The label can be a ligand or dye, for example, a fluorescent dye. The fluorescent dye can be a fluorophore selected from FAM, Bodipy, TAMRA and Alexa or others disclosed herein. The linker can be cleavable by a protease such as proteinase K, trypsin, chymotrypsin, subtilisin, V8 protease or others disclosed herein. The kit can further comprise a protease having activity to cleave the peptide linker. Thus, the kit can contain a protease specific for the peptide linker of the nucleoside or nucleotide in the kit. A removable blocking group on the nucleoside or nucleotide can be a phosphate. In a kit containing, a nucleoside or nucleotide containing phosphate as the removable blocking group, a phosphatase can also be included to conveniently remove the phosphate blocking group. It is understood that the kit can contain appropriate nucleoside or nucleotides and/or reagents for cleaving a cleavable linker, if contained in the nucleoside or nucleotides of the kit, and/or reagents for removing a removable blocking group. In a particular embodiment, the kit contains four nucleosides or nucleosides, either A, G, T and C, or A, G, U and C, or derivatives thereof, as disclosed herein, including deoxy forms, such that a complementary sequence of a target nucleic acid sequence can be synthesized by a nucleotide incorporating catalyst, with each of the four nucleosides or nucleotides containing a distinguishable label such as a dye, for example, a fluorescent dye, so that each of the four nucleosides or nucleotides can be identified by its respective label, as disclosed herein.

Analytical methods set forth herein can be carried out on a solid-phase support, for example, as indicated above. Accordingly, oligonucleotides, nucleotides or nucleosides described herein can be attached to a solid-phase support, used to modify a molecule attached to a solid support or non-covalently bound to a molecule on a solid support.

As used herein, the term "solid support" is intended to mean a substrate and includes any material that can serve as a solid or semi-solid foundation for attachment of capture probes, other nucleic acids and/or other polymers, including biopolymers. A solid support of the invention is modified, for example, or can be modified to accommodate attachment of nucleic acids by a variety of methods well known to those skilled in the art. Exemplary types of materials comprising solid supports include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtier plates. Specific types of exemplary plastics include acrylics, polystyrene, copolymers of styrene and other materials, polypropylene, polyethylene, polybutylene, polyurethanes and Teflon™. Specific types of exemplary silica-based materials include silicon and various forms of modified silicon.

The term "microsphere," "bead" or "particle" refers to a small discrete particle as a solid support of the invention. Populations of microspheres can be used for attachment of populations of capture probes. The composition of a microsphere can vary, depending for example, on the format, chemistry and/or method of attachment and/or on the method of nucleic acid synthesis. Exemplary microsphere compositions include solid supports, and chemical functionalities imparted thereto, used in polypeptide, polynucleotide and/or organic moiety synthesis. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as any other materials which can be found described in, for example, "*Microsphere Detection Guide*" from Bangs Laboratories, Fishers Ind., which is incorporated herein by reference.

The geometry of a particle, bead or microsphere also can correspond to a wide variety of different forms and shapes. For example, microspheres used as solid supports of the invention can be spherical, cylindrical or any other geometrical shape and/or irregularly shaped particles. In addition, microspheres can be, for example, porous, thus increasing the surface area of the microsphere available for capture probe or other nucleic acid attachment. Exemplary sizes for microspheres used as solid supports in the methods and compositions of the invention can range from nanometers to millimeters or from about 10 nm-1 mm. Particularly useful sizes include microspheres from about 0.2 µm to about 200 µm and from about 0.5 µm to about 5 µm being particularly useful.

In particular embodiments, microspheres or beads can be arrayed or otherwise spatially distinguished. Exemplary bead-based arrays that can be used in the invention include, without limitation, those in which beads are associated with a solid support such as those described in U.S. Pat. No. 6,355,431 B1, US 2002/0102578 and PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. patent application Nos. US 2004/0263923, US 2004/0233485, US 2004/0132205, or US 2004/0125424, each of which is incorporated herein by reference. Beads can be associated with discrete locations via covalent bonds or other non-covalent interactions such as gravity, magnetism, ionic forces, van der Waals forces, hydrophobicity or hydrophilicity. However, the sites of an array of the invention need not be discrete sites. For example, it is possible to use a uniform surface of adhesive or chemical functionalities that allows the attachment of particles at any position. Thus, the surface of an array substrate can be modified to allow attachment or association of microspheres at individual sites, whether or not those sites are contiguous or non-contiguous with other sites. Thus, the surface of a substrate can be modified to form discrete sites such that only a single bead is associated with the site or, alternatively, the surface can be modified such that a plurality of beads populates each site.

Beads or other particles can be loaded onto array supports using methods known in the art such as those described, for example, in U.S. Pat. No. 6,355,431, which is incorporated herein by reference. In some embodiments, for example when chemical attachment is done, particles can be attached to a support in a non-random or ordered process. For example, using photoactivatible attachment linkers or photoactivatible adhesives or masks, selected sites on an array support can be sequentially activated for attachment, such that defined populations of particles are laid down at defined positions when exposed to the activated array substrate. Alternatively, particles can be randomly deposited on a substrate. In embodiments where the placement of probes is random, a coding or decoding system can be used to localize and/or identify the probes at each location in the array. This can be done in any of a variety of ways, for example, as described in U.S. Pat. No. 6,355,431 or WO 03/002979, each of which is incorporated herein by reference. A further encoding system that is useful in the invention is the use of diffraction gratings as described, for example, in US Pat. App. Nos. US 2004/0263923, US 2004/0233485, US 2004/0132205, or US 2004/0125424, each of which is incorporated herein by reference.

An array of beads useful in the invention can also be in a fluid format such as a fluid stream of a flow cytometer or similar device. Exemplary formats that can be used in the invention to distinguish beads in a fluid sample using microfluidic devices are described, for example, in U.S. Pat. No. 6,524,793, which is incorporated herein by reference. Commercially available fluid formats for distinguishing beads include, for example, those used in XMAP™ technologies from Luminex or MPSS™ methods from Lynx Therapeutics.

Any of a variety of arrays known in the art can be used in the present invention. For example, arrays that are useful in the invention can be non-bead-based. A particularly useful array is an Affymetrix™ GeneChip™ array. GeneChip™ arrays can be synthesized in accordance with techniques sometimes referred to as VLSIPS™ (Very Large Scale Immobilized Polymer Synthesis) technologies. Some aspects of VLSIPS™ and other micro array and polymer (including protein) array manufacturing methods and techniques have been described in U.S. patent Ser. No. 09/536,841, international Publication No. WO 00/58516; U.S. Pat. Nos. 5,143,854, 5,242,974, 5,252,743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752; and in PCT Applications Nos. PCT/US99/00730 (International Publication No. WO 99/36760) and PCT/US01/04285, each of which is incorporated herein by reference. Such arrays can hold over 500,000 probe locations, or features, within a mere 1.28 square centimeters. The resulting probes are typically 25 nucleotides in length. If desired, a highly efficient synthesis in which substantially all of the probes are full length can be used.

A spotted array can also be used in a method of the invention. An exemplary spotted array is a CodeLink™ Array available from Amersham Biosciences CodeLink™ Activated Slides are coated with a long-chain, hydrophilic polymer containing amine-reactive groups. This polymer is covalently crosslinked to itself and to the surface of the slide. Probe attachment can be accomplished through covalent interaction between the amine-modified 5' end of the oligonucleotide probe and the amine reactive groups present in the polymer. Probes can be attached at discrete locations using spotting pens. Such pens can be used to create features having a spot diameter of, for example, about 140-160 microns. In a particular embodiment, nucleic acid probes at each spotted feature can be 30 nucleotides long.

Another array that is useful in the invention is one manufactured using inkjet printing methods such as SurePrint™ Technology available from Agilent Technologies. Such methods can be used to synthesize oligonucleotide probes in situ or to attach presynthesized probes having moieties that are reactive with a substrate surface. A printed microarray can contain 22,575 features on a surface having standard slide dimensions (about 1 inch by 3 inches). Typically, the printed probes are 25 or 60 nucleotides in length.

It will be understood that the specific synthetic methods and probe lengths described above for different commercially available arrays are merely exemplary. Similar arrays can be made using modifications of the methods and probes having other lengths such as those set forth elsewhere herein can also be placed at each feature of the array.

Those skilled in the art will know or understand that the composition and geometry of a solid support of the invention can vary depending on the intended use and preferences of the user. Therefore, although microspheres and chips are exemplified herein for illustration, given the teachings and guidance provided herein, those skilled in the art will understand that a wide variety of other solid supports exemplified for other embodiments herein or well known in the art also can be used in the methods and/or compositions of the invention.

Capture probes or templates to be sequenced, for example, can be attached to a solid support using any of a variety of methods well known in the art. Such methods include for example, attachment by direct chemical synthesis onto the solid support, chemical attachment, photochemical attachment, thermal attachment, enzymatic attachment and/or absorption. These and other methods are well known in the art and applicable for attachment of capture probes in any of a variety of formats and configurations. The resulting probes can be attached to a solid support via a covalent linkage or via non-covalent interactions. Exemplary non-covalent interactions are those between a ligand-receptor pair such as streptavidin (or analogs thereof) and biotin (or analogs thereof) or between an antibody and epitope. Once attached to the first solid support, the target sequence, probe or primer is amenable for use in the methods as described herein.

Several of the methods set forth herein can be carried out in a multiplex format in which several different reactions are carried out simultaneously and in the same vessel or on the same substrate. As exemplified above, several methods such as primer extension methods, ligation methods or sequencing methods can be carried out in multiplex formats, for example, using arrays. Oligonucleotides and nucleotides having a reversible blocking group on a 2', 3' or 4' hydroxyl, a peptide linked label or a combination thereof are particularly useful in multiplex methods because such molecules can be introduced, detected and moieties removed using uniform conditions across a plurality of reaction centers. For example, using uniform conditions nucleotides can be introduced to specific sites on an array; sites having the specific nucleotides can be identified; and blocking groups, labels or both removed. Methods set forth herein can be carried out at multiplex levels in which at least 10, 100, 1000, $1 \times 10^4$, $1 \times 10^5$, $1 \times 10^6$, $1 \times 10^7$ or more different reactions occur simultaneously in the same vessel or on the same substrate.

It is understood that modifications which do not substantially affect the activity of the various embodiments of this invention are also provided within the definition of the invention provided herein. Accordingly, the following examples are intended to illustrate but not limit the present invention.

EXAMPLE I

Synthesis of Nucleotides

This example describes the synthesis of exemplary nucleotides useful in the invention.

An exemplary 2' reversible terminator with a phosphate group at the 2' position was synthesized, as shown in FIG. 1B. Synthesis of various nucleotides is described in more detail below.

Synthesis of 2'-Phosphate UTP

For synthesis of 2'-phospho UTP, 100 mg of 3'phosphate CPG (Glen Research), 43 umol/g, was placed into a 3 ml fritted syringe. The syringe was washed 3 times with 3% trichloroacetic acid/dichloromethane (TCA/DCM) solution, 2 min, followed by washing 6 times with 2 ml acetonitrile. A volume of 1.5 ml of 0.1M solution of 5'-DMT-3'-tBDsilyl-ribo uridine CED phorphoramidite (Catalog No. ANP-5674, ChemGenes; Wilmington Mass.) in acetonitrile was mixed with 1.5 ml of 0.25 M 4,5-dicyanoimidazole (DCI) in acetonitrile and added to the reaction vessel. The reaction was carried out for 10 min. The syringe was washed with 2 ml acetonitrile, and the reaction repeated for 10 min. The syringe was washed 6 times with 2 ml acetonitrile. An oxidizing solution (0.02 M $I_2$ in Py/THF/$H_2O$)(Glen Research) was added and reacted for 2 min. The syringe was washed 6 times with 2 ml acetonitrile, 3 times with 3% TCA/DCM solution for 2 min, and 6 times with 2 ml acetonitrile. A volume of 2 ml pyridine:dioxane mixture (1:3) was added. A volume of 500 µl of 1 M of 2-chloro-4H-1,3,2-Benzodioxaphosphor-4-one (Aldrich) in dioxane was added and reacted for 15 min. The syringe was washed 3 times with 2 ml dioxane and 3 times with 2 ml acetonitrile. A volume of 1.5 ml of 0.5M tributylammonium pyrophosphate (Aldrich) in DMF was added. A volume of 1 ml of tri-n-butylamine (Aldrich) was added and reacted for 20 min. The syringe was washed 3 times with 2 ml DMF and 3 times with 2 ml acetonitrile. Oxidizing solution (0.02M $I_2$ in Py/THF/$H_2O$) was added and reacted for 2 min. The syringe was washed 6 times with 2 ml acetonitrile. A volume of 2 ml of 28% aqueous ammonia solution (Aldrich) was added and reacted overnight at room temperature. The supernatant was removed, and the product dried on a Speed Vac. A volume of 500 µl of 1M tetra-n-butyl ammonium fluoride (TBAF)/THF was added and reacted overnight at room temperature. The product was dried on a SpeedVac and purified by HPLC.

Synthesis of 3'-Phosphate dTTP

For synthesis of 3' phosphate dTTP, 50 mg of 3' phosphate CPG (Glen Research), 43 umol/g, was placed into a 3 ml fritted syringe. The syringe was washed 3 times with 3% TCA/DCM solution for 2 mm followed by washing 6 times with 2 ml acetonitrile. A volume of 1.5 ml of 0.1M solution of dT-phosphoramidite (Glen Research) in acetonitrile was mixed with 1.5 ml of 0.25M DCI in acetonitrile, added to the reaction vessel and reacted for 10 mm. The syringe was washed with 2 ml acetonitrile. The reaction was repeated for 10 min. The syringe was washed 6 times with 2 ml acetonitrile. Oxidizing solution (0.02M $I_2$ in Py/THF/$H_2O$) was added and reacted for 2 min. The syringe was washed 6 times with 2 ml acetonitrile, 3 times with 3% TCA/DCM solution for 2 min. and 6 times with 2 ml acetonitrile. A volume of 2 ml pyridine:dioxane mixture (1:3) was added. A volume of 500 µl of 1 M of 2-chloro-4H-1,3,2-Benzodioxaphosphor-4-one (Aldrich) in dioxane was added and reacted for 15 min. The syringe was washed 3 times with 2 ml dioxane and 3 times with 2 ml acetonitrile. A volume of 1.5 ml of 0.5 M tributylammonium pyrophosphate (Aldrich) in DMF was added. A volume of 1 ml of tri-n-butylamine (Aldrich) was added and reacted for 20 min. The syringe was washed 3 times with 2 ml DMF and 3 times with 2 ml acetonitrile. Oxidizing solution (0.02M $I_2$ in Py/THF/$H_2O$) was added and reacted for 2 min. The syringe was washed 6 times with 2 ml acetonitrile. A volume of 2 ml of 28% aqueous ammonia solution (Aldrich) was added and reacted overnight at room temperature. The supernatant was removed, and the product dried on SpeedVac. HPLC purify.

Synthesis of Aldehyde-Modified dTTP and dCTP

For synthesis of aldehyde-modified dTTP and dCTP, 45 µl of 0.1M solution of 5-aminoallyl-2'-dUTP (or dCTP) from Trilink Biotechnoligies was used. A volume of 60 µl of 1M triethylammonia bicarbonate buffer (Fluka) was added. A volume of 150 µl of DMF was added and mixed well. A volume of 100 µl of 0.4M solution of SFB reagent (SoluLink Biotechnologies) in DMF was added, mixed and reacted overnight at room temperature. The products were HPLC purified.

Synthesis of Amino-Modified dGTP and dATP

For synthesis of amino-modified dGTP and dATP, 0.08 mmol of 7-Deaza-7-phthalylpropargyl-dA (or 7-Deaza-7-phthalylpropargyl-dG) from ChemBiotech was used and dried overnight in vacuum under $P_2O_5$. A volume of 267 µl of 1M trimethylphosphate (Aldrich) was added while stirring. The suspension was cooled to 0° C. A volume of 12 µl of $POCl_3$ was added and stirred at 0° C. for 3 hours. A volume of 2 ml of 0.5M tributylammonia pyrophosphate (Aldrich) in DMF was mixed with 500 µl of tri-n-butylamine (Aldrich), added to the reaction vessel and reacted for 20 min. A volume of 6.7 ml of 0.1 M triethylammonium bicarbonate buffer (Fluka) was added and kept at room temperature for 45 min. A volume of 6.7 ml of 28% aqueous ammonia solution (Aldrich) was added and reacted for 3 hours at room temperature. The product was dried on a SpeedVac and HPLC purified.

Synthesis of Aldehyde-Modified dGTP and dATP

For synthesis of aldehyde-modified dGTP and dATP, a volume of 45 µl of 0.1M solution of amino-GTP (or amino ATP) was used. A volume of 60 µl of 1M Triethylammonia bicarbonate buffer (Fluka) was added. A volume of 150 ul of DMF was added and mixed well. A volume of 100 µl of 0.4M solution of succinimidyl 4-formylbenzoate (SFB) reagent (SoluLink Biotechnologies) in DMF was added, mixed and reacted overnight at room temperature. The products were HPLC purified.

The following nucleotides have been synthesized: dUTP-FAM, dCTP-FAM, dATP-FAM, dGTP-FAM, dUTP-BodipyFL, dCTP-BodipyTMR, dUTP-BodipyTR, dATP-Alexa660, and dGTP-Alexa750 (see FIGS. 10 and 12).

EXAMPLE II

Enzymatic Removal of a Blocking Group from a Reversible Terminator

This example describes removal of a blocking group from an exemplary 2' reversible terminator.

A 2' reversible terminator having a phosphate blocking group at the 2' position, as shown in FIG. 1B, was used. The 2' reversible terminator was incubated with alkaline phosphatase. The results show that the phosphate group can be quantitatively removed using alkaline phosphatase in less than one minute in aqueous buffer at room temperature. Briefly, 2' reversible terminator ribonucleotide was incorporated into a 15-mer primer, annealed to a 42-mer template oligonucleotide, and phosphate removed in the duplex by incubation with calf intestinal alkaline phosphatase (2 mU/µl; USB) for 10 minutes at 37° C.

EXAMPLE III

Identification and Optimization of Enzymatically Cleavable Peptide Linkers

This example describes the identification of exemplary peptide linkers cleavable by proteases.

Peptide synthesis can be carried out using standard Fmoc solid phase peptide synthesis. After synthesis, the peptides were cleaved from the support and the protecting groups removed using 95% TFA with scavengers. The peptides were then precipitated with ethyl ether, washed and dried. The peptides wore then dissolved in an appropriate solvent and analyzed by HPLC and mass spectroscopy for quality analysis.

Cleavage data has been generated for 1000 different peptides for subtilisin A, chymotrypsin and proteinase K. Cleavage of a set of exemplary peptides is shown in FIG. 3. Assays were carried out essentially as described previously in U.S. publication 2006/0216721, which is incorporated herein by reference.

Figure 4:
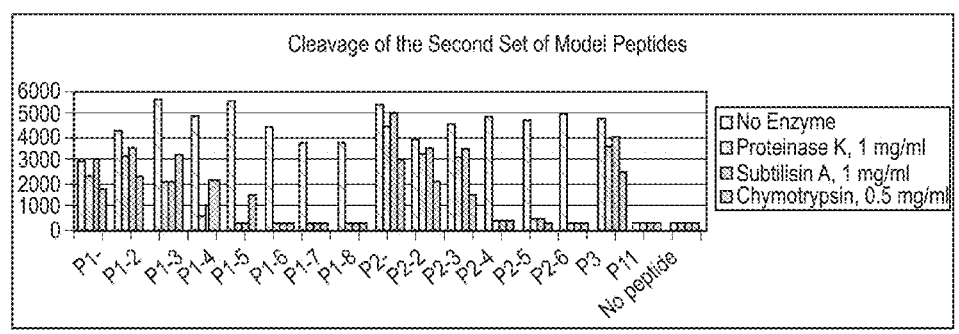
FIG. 4 shows optimization of a peptide linker. Various sequences based on peptide P7 of FIG. 3 were synthesized and tested for cleavage with proteinase K, subtilisin and chymotrypsin.

Among the 10 peptide sequences, one peptide was selected for further optimization to reduce peptide length. Shown in FIG. 4 are various peptides based on the 13-mer peptide identified in FIG. 3 as the best performing peptide (P7). Various lengths of peptides were synthesized and tested for effectiveness as a substrate for proteinase K, subtilisin and chymotrypsin.

Figure 5:
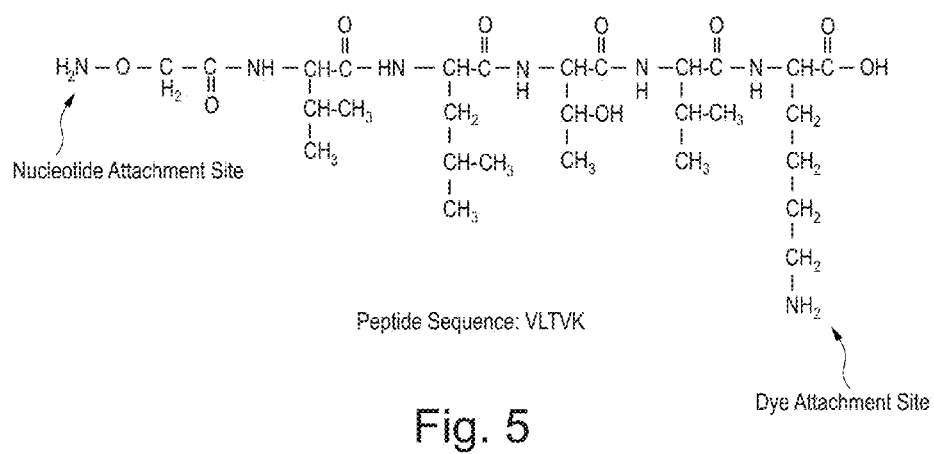
FIG. 5 shows the structure of an exemplary cleavable peptide linker.

One model peptide containing 4 amino acids was selected to link the nucleoside and dye molecules. Shown in FIG. 5 is an exemplary 4 amino acid peptide VLTV that is effectively cleaved by a protease, with the nucleotide attachment site and dye attachment site shown. In this example, the dye attachment site is through a lysine attached to the C-terminus of the peptide linker.

EXAMPLE IV

Synthesis of Enzymatically Cleavable Peptide Linked Nucleotides

This example describes a synthetic scheme for an exemplary nucleotide linked to a dye via a cleavable peptide linker.

The VLTK 4-mer peptide linker was synthesized to generate FAM-dUTP with a peptide linker. The synthesis scheme is outlined in FIG. 6. Although shown for dUTP, a similar reaction scheme can be used to generate all four dNTPs.

Briefly, for attaching peptides to aldehyde-modified dTTP, dCTP, dGTP and dATP, a volume of 60 µl of 0.02M solution of aldehyde-modified dTTP (or dCTP, dGTP and dATP) was used (see Example I for synthesis). A volume of 40 µl of 1M Na citrate buffer, pH 5.0, was added. A volume of 100 µl of 0.02M peptide solution in dimethylsulfoxide (DMSO) was added, mixed and reacted overnight at room temperature. The products were HPLC purified.

FIG. 7 shows HPLC analysis of modified dUTPs. The amino-dUTP, aldehyde-dUTP and FAM-peptide dUTP, as shown in FIG. 6, were analyzed. A DNAPac PA-100 (Dionex) HPLC column was used. The nucleotides were eluted with a linear gradient of triethylammonium bicarbonate buffer (Fluka) over 15 minutes starting from 0.025M to 0.5M.

The peptide linked dUTP was tested based on its incorporation using commercially available polymerase in both solution and on BeadArray™ (Illumina, San Diego Calif.). Shown in FIG. 8 is gel analysis of solution phase incorporation. The reaction was carried out with the components as indicated in FIG. 8 and analyzed by gel electrophoresis. Briefly, 300 nM 22-mer FAM-labeled oligonucleotide primer was annealed to 500 nM 43-mer unlabeled template in 10 mM Tris-acetate pH 7.5, 0.4 mM EDTA, 1.4 mM $MgCl_2$ by heating the solution to 95° C. and allowing it to cool slowly to room temperature. Appropriate nucleotides were added for a final concentration of 5 µM. A 1:500 dilution of Klenow (lacking 3'-5' exonuclease activity, NEB) was added. The reaction proceeded at 37° C. for 30 min. Reactions were quenched by addition of loading buffer containing 95% formamide, 25 mM EDTA. Samples were loaded onto a 20% polyacrylamide gel electrophoresis (PAGE) sequencing gel and run at 60° C.

FIG. 9 shows analysis of incorporation of FAM-dUTP on a BeadArray™. Briefly, the array was washed with 100% formamide for 1 mm followed by washing 2 times with Hybe Buffer (60 mM potassium phosphate, pH 7.6, 0.6 mM NaCl, 0.05% Tween-20, 40% formamide) for 1 min. 5 nM DNA with attached peptides containing biotin residue was hybridized in Hybe Buffer for 30 min at room temperature. After hybridization, the array was washed 1 time with Hybe Buffer, washed 6 times with PBI buffer (Illumina), and washed 1 time with 50 mM Tris-HCl buffer, pH 7.8. The array was incubated with subtilisin A protease (1 mg/ml) in 50 mM Tris-HCl buffer, pH 7.8 for 1 min. The array was washed 6 times with phosphate buffered saline (PBS), pH 7.4/0.1% Tween buffer. The array was incubated with a solution of LMM (Illumina) for 30 min at room temperature. The array was washed 6 times with PBS/Tween buffer. The array was imaged on a BeadArray™ (Illumina) reader.

FIGS. 8 and 9 show that 1) the peptide linked dUTP can be incorporated onto primers with specificity; and 2) after the incorporation, the dye molecule can be removed by enzymatic peptide cleavage.

In addition to the FAM-dNTP shown in FIG. 6, other fluorescent dyes can similarly be used with the VLTK peptide linker. Exemplary fluorophores include Bodipy FL, Bodipy TMR-X, Bodipy R6G, and Bodipy TR-X, as illustrated in FIG. 10, or fluorescein, FAM, rhodamine, TAMRA, AlexaFluor-660 and AlexFluor-750, as shown in FIG. 12. It will be understood that derivatives of the fluorophores exemplified herein can also be used, so long as they produce fluorescent signals having desired properties to suit a particular embodiment. If desired, a different fluorophore can be added to each of the four nucleotides such that the nucleotides can be used simultaneously and be independently detected. FIGS. 11 and 13 show the emission spectra of the fluorophores shown in FIGS. 10 and 12, respectively. As shown in these figures, the fluorophores are selected for each of the four nucleotides so that the emission spectra of each fluorophore are sufficiently non-overlapping so that each fluorophore can be detected simultaneously.

Throughout this application various publications have been referenced. The disclosures of these publications in their entireties are hereby incorporated by reference in this application in order to more fully describe the state of the art to which this invention pertains. Although the invention has been described with reference to the examples provided above. It should be understood that various modifications can be made without departing from the spirit of the invention.

What is claimed is:

1. A blocked nucleotide comprising a sugar moiety and a base moiety, wherein said base moiety is linked to a label by linker, and
   wherein, attached at the 4' position of said sugar moiety, is a blocking group comprising a phosphate.

2. The nucleotide of claim 1, wherein said label is a fluorescent dye.

3. The nucleotide of claim 1, wherein said label comprises a ligand.

4. The nucleotide of claim 1, wherein said nucleotide molecule is a nucleotide triphosphate.

5. The nucleotide of claim 1, wherein said blocking group is cleavable by enzymatic, photolytic and/or chemical cleavage.

6. The nucleotide of claim 1, wherein the sugar moiety further comprises a blocking group attached at the 2' position.

7. The nucleotide of claim 1, wherein the linker comprises an enzymatically cleavable peptide linker.

8. The nucleotide of claim 7, wherein said enzymatically cleavable peptide linker can be cleaved by a protease.

9. A nucleic acid molecule comprising the nucleotide of claim 1.

10. The nucleic acid molecule of claim 9, wherein said nucleotide is at the 5' or 3' terminus of the nucleic acid.

11. A kit comprising the nucleotide of claim 1 and polymerase configured to incorporate the nucleotide into a growing nucleic acid molecule.

12. The kit of claim 11, wherein linker comprises an enzymatically cleavable peptide linker and wherein the kit further comprises an enzyme configured to cleave the linker.

13. A blocked nucleotide comprising a sugar moiety and a base moiety, wherein said base moiety is linked to a label by linker,
   wherein, attached at the 4' position of said sugar moiety, is a blocking group comprising —$CH_2$—CH=$CH_2$, —$CH_2$—$N_3$, —$CH_2$—S—S-tBu, —$CH_2$—S-Me, —$CH_2$—O—$CH_2$—$CH_2$—CN, —$CH_2$—$CH_2$—CN, —C(O)—$CH_3$, —$CH_3$, 2-nitrobenzyl, tetrahydropyran, 4-nitrobenzoyl, 2-aminobenzoyl, —C(O)-linker-dye, 2-nitrobenzyl-linker-dye, —C(O)—O—$CH_2$—CH=CH-linker-dye, —NH—C(O)—$CH_3$, —F, —$NH_2$, phosphate, or sulfate; and
   wherein the linker comprises an enzymatically cleavable peptide linker.

14. The nucleotide of claim 13, wherein said blocking group comprises a phosphate.

15. The nucleotide of claim 13, wherein said label is a fluorescent dye.

16. The nucleotide of claim 13, wherein said label comprises a ligand.

17. The nucleotide of claim 13, wherein said nucleotide molecule is a nucleotide triphosphate.

18. The nucleotide of claim 13, wherein said blocking group is cleavable by enzymatic, photolytic and/or chemical cleavage.

19. The nucleotide of claim 13, wherein the sugar moiety further comprises a blocking group attached at the 2' position.

20. A nucleic acid molecule comprising the nucleotide of claim 13.

\* \* \* \* \*

SEQUENCE LISTING

```
<160> NUMBER OF SEQ ID NOS: 26

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

-continued

Leu Val Pro Arg Gly Ser
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: variable amino acid

<400> SEQUENCE: 2

Ile Glu Gly Arg Xaa
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid

<400> SEQUENCE: 3

Asp Asp Asp Asp Lys Xaa
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Asn Leu Tyr Phe Gln Gly
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Glu Val Leu Phe Gln Gly Pro
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Leu Glu Val Leu Phe Gln Gly Pro
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Leu Thr Val
 1

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His His His His His Leu Leu Val Tyr Gly Gly Gly Gly
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His His His His His Leu Asn Ala Gly Phe Thr Ala Ser
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His His His His His Ser Leu Ala Tyr Tyr Thr Ala Gly
 1               5                  10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His His His His His Ile Thr Val Gln Thr Val Thr Trp
 1               5                  10

<210> SEQ ID NO 12
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 12

His His His His His Leu Gly Leu Ala Arg Gly Gly Gly
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His His His His His Leu Gly Arg Leu Leu Val Val Tyr
 1               5                  10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His His His His His Ala Thr Val Leu Thr Val Ala Leu
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His His His His His Ser Gln Asn Tyr Val Ile Val Gly
 1               5                  10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His His His His His Ile Glu Pro Arg Ser Phe Ser Gln
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His His His His His Leu Ser Pro Arg Thr Phe His Pro
 1               5                  10
```

```
<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His His His His His His Gly Ala Gly Ala
 1               5                  10

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Val Ala Leu
 1

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Thr Val Ala Leu
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Leu Thr Val Ala Leu
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Val Leu Thr Val Ala Leu
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Ala Thr Val Leu Thr Val Ala Leu
  1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Leu Thr Val
  1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Val Leu Thr Val
  1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Thr Val Leu Thr Val
  1               5
```